(12) United States Patent
Tschentscher et al.

(10) Patent No.: US 9,040,265 B2
(45) Date of Patent: May 26, 2015

(54) OXIDOREDUCTASES FOR THE STEREOSELECTIVE REDUCTION OF KETO COMPOUNDS

(75) Inventors: Anke Tschentscher, Eltville (DE); Antje Gupta, Wiesbaden (DE); Maria Bobkova, Idstein (DE)

(73) Assignee: IEP GMBH, Wiesbaden (DE)

( * ) Notice: Subject to any disclaimer, the term of this patent is extended or adjusted under 35 U.S.C. 154(b) by 432 days.

(21) Appl. No.: 13/280,876

(22) Filed: Oct. 25, 2011

(65) Prior Publication Data

US 2014/0017743 A1    Jan. 16, 2014

Related U.S. Application Data

(63) Continuation of application No. 11/996,968, filed as application No. PCT/EP2006/007150 on Jul. 20, 2006, now abandoned.

(30) Foreign Application Priority Data

Jul. 27, 2005  (AT) .................................. 1261/2005

(51) Int. Cl.
| | |
|---|---|
| *C12P 7/62* | (2006.01) |
| *C12N 9/02* | (2006.01) |
| *C12P 7/04* | (2006.01) |
| *C12P 7/42* | (2006.01) |
| *C12P 7/02* | (2006.01) |

(52) U.S. Cl.
CPC ............. *C12P 7/62* (2013.01); *C12N 9/0004* (2013.01); *C12N 9/0008* (2013.01); *C12P 7/04* (2013.01); *C12P 7/42* (2013.01); *C12P 7/02* (2013.01)

(58) Field of Classification Search
None
See application file for complete search history.

(56) References Cited

U.S. PATENT DOCUMENTS

| | | | |
|---|---|---|---|
| 5,200,355 | A | 4/1993 | Choi et al. |
| 5,385,833 | A | 1/1995 | Bradshaw et al. |
| 5,523,223 | A | 6/1996 | Kula et al. |
| 5,523,233 | A | 6/1996 | Chartrain et al. |
| 5,763,236 | A | 6/1998 | Kojima et al. |
| 6,037,158 | A | 3/2000 | Hummel et al. |
| 2004/0214297 | A1 | 10/2004 | Davis et al. |
| 2004/0265978 | A1 | 12/2004 | Gupta et al. |
| 2005/0037946 | A1 | 2/2005 | Stagliano et al. |
| 2005/0191735 | A1 | 9/2005 | Bobkova et al. |
| 2006/0195947 | A1 | 8/2006 | Davis et al. |
| 2007/0243594 | A1 | 10/2007 | Gupta et al. |
| 2009/0280525 | A1 | 11/2009 | Gupta et al. |

FOREIGN PATENT DOCUMENTS

| | | |
|---|---|---|
| DE | 19610984 | 9/1997 |
| DE | 10119274 | 10/2002 |
| DE | 10300335 | 7/2004 |
| DE | 10327454 | 1/2005 |
| EP | 1 179 595 | 2/2002 |
| EP | 1731618 | 12/2006 |
| JP | 03127998 | 5/1991 |
| JP | 07-231785 | 5/1995 |
| WO | 02/086126 | 10/2002 |
| WO | 03/091423 | 11/2003 |
| WO | 2004/111083 | 12/2004 |

OTHER PUBLICATIONS

Amy E. Krafft et al., Purification and Characterization of a Novel Form of 20a-Hydroxysteroid Dehydrogenase from *Clostridium scindens*, Journal of Bacteriology, Jun. 1989, 2925-2932, American Society for Microbiology.

Ayako Inazu et al., Purification and characterization of a novel dimeric 20a-hydroxysteroid dehydrogenase from *Tetrahymena pyriformis*, Biochem. J., 1994, 195-200, 297.

Carrea, G. et al.: Enzymatic oxidoreduction of steroids in two-phase systems: effects of organic solvents on enzyme kinetics and evaluation of the performance of different reactors, Enzyme and Microbial Technology, (1998), vol. 10, No. 6, pp. 333-340.

Cremonesi, P. et al.: Enzymatic Dehydrogenation of Steroids by beta-Hydroxysteroid Dehydrogenase in a Two-Phase system, Archives of Biochemistry and Biophysics, vol. 159, (1973), pp. 7-10.

Donna W. Payne et al., Isolation of Novel Microbial 3a-, 3B-, and 17B-Hydroxysteroid Dehydrogenases, The Journal of Biological Chemistry, 1985, 13648-13655, vol. 260, No. 25, Issue of Nov. 5, The American Society of Biological Chemists, Inc.

Edward S. Szymanski et al., 20B-Hydroxysteroid Oxidoreductase, Kinetics and Binding of Corticosteroids and Corticosteroid-21-Aldehydes, The Journal of Biological Chemistry, 1977, 205-211, vol. 252, No. 1, Issue of Jan. 10.

(Continued)

*Primary Examiner* — Nashaat Nashed
(74) *Attorney, Agent, or Firm* — Workman Nydegger

(57) ABSTRACT

The invention relates to a process for the enantioselective enzymatic reduction of a keto compound to the corresponding chiral hydroxy compound, wherein the keto compound is reduced with an oxidoreductase in the presence of a cofactor, and is characterized in that an oxidoreductase is used which has an amino acid sequence in which (a) at least 70% of the amino acids are identical to the amino acids of one of the amino acid sequences SEQ ID No 1, SEQ ID No 6 and SEQ ID No 8, or (b) at least 55% of the amino acids are identical to the amino acids of the amino acid sequence SEQ ID No 2, or (c) at least 65% of the amino acids are identical to the amino acids of the amino acid sequence SEQ ID No 3, or (d) at least 75% of the amino acids are identical to the amino acids of the amino acid sequence SEQ ID No 4, or (e) at least 65% of the amino acids are identical to the amino acids of the amino acid sequence SEQ ID No 5, or (f) at least 50% of the amino acids are identical to the amino acids of the amino acid sequence SEQ ID No 7, or (g) at least 72% of the amino acids are identical to the amino acids of the amino acid sequence SEQ ID No 129.

13 Claims, No Drawings

(56) References Cited

OTHER PUBLICATIONS

Eiji Itagaki et al., Purification and Characterization of 17B-Hydroxysteroid Dehydrogenase from *Cylindrocarpon radicicola*, J. Biochem, 1988, 1039-1044, vol. 103, No. 6.

Flynn et al. J. Pharm. Sci. (1979) 68(9): 1090-1097.

G. Carrera et al., Enzymatic Preparation of 12-Ketochenodeoxycholic Acid with NADP Regeneration, Biotechnology and Bioengineering, 1984, pp. 560-563, vol. XXVI, John Wiley & Sons, Inc.

Giacomo Carrera et al., Enzymatic reduction of dehydrocholic acid to 12-ketochenodeoxycholic acid with NADH regeneration, Enzyme Microb. Technol., Jul. 1984, 307-310, vol. 6, Butterworth & Co. Ltd.

Guangming Xiong et al., Regulation of the Steroid-inducible 3a-Hydroxysteroid Dehydrogenase/Carbonyl Reductase Gene in *Comamonas testosteroni*, The Journal of Biological Chemistry, 2001, 9961-9970, vol. 276, No. 13, Issue of Mar. 30, The American Society for Biochemistry and Molecular Bioloby, Inc.

J.H. Abalain, Cloning, DNA Sequencing and Expression of (3-17)B Hydroxysteroid Dehydrogenase from *Pseudomonas testosteroni*, J. Steroid Biochem. Molec. Biol., 1993, 133-139, vol. 44, No. 2.

James P. Coleman, Characterization and Regulation of the NADP-Linked 7a-Hydroxysteroid Dehydrogenase Gene from *Clostridium sordellii*, Journal of Bacteriology, Aug. 1994, 4865-4874, vol. 176, No. 16, American Society for Microbiology.a.

Karsten Niefind et al., Crystallization and preliminary characterization of crystals of R-alcohol dehydrogenase from *Lactobacillus brevis*, Biological Crystallography, Acta Cryst., 2000, 1696-1698, D56.

Manfred Braun et al., 12a-Hydroxysteroid dehydrogenase from *Clostridium* group P, strain C 48-50, Production, purification and characterization, Eur. J. Biochem., 1991, 439-450, 196, EEBS.

Michael J. Bennett, Cloning and Characterization of the NAD-Dependent 7a-Hydroxysteroid Dehydrogenase from *Bacteroides fragilis*, Current Microbiology, 2003, 475-484, vol. 47, Springer-Verlag, New York Inc.

Paloma De Prada et al., Purification and characterization of a novel 17a-hydroxysteroid dehydrogenase from an intestinal *Eubacterium* sp. VPI 12708, Journal of Lipid Research, 1994, 922-929, vol. 35.

Paola Pedrini et al., *Xanthomonas maltophilia* CBS 897.97 as a source of new 7B-and 7a-hydroxysteroid dehydrogenases and cholylglycine hydrolase: Improved biotransformations of bile acids, Steroids, 2006, 189-198, 71.

Pietro Cremonesi et al., Enzymatic Dehydrogenation of Testosterone Coupled to Pyruvate Reduction in a Two-Phase System, J. Biochem., 1974, 401-405, 44.

Pietro Cremonesi et al., Enzymatic Preparation of 20B-Hydroxysteroids in a Two-Phase System, Biotechnology and Bioengineering, 1975, pp. 1101-1108, vol. XVII, John Wiley & Sons, Inc.

Richard M. Schultz, 3(17)B-Hydroxysteroid Dehydrogenase of *Pseudomonas testosteroni*, A Convenient Purification and Demonstration of Multiple Molecular Forms, The Journal of Biological Chemistry, 1977, 3775-3783, vol. 252, No. 11, Issue of Jun. 10.

Riva, S. et al.: Enzymatic alpha/beta Inversion of C-3 Hydroxyl of Bile Acids and Study of the Effects of Organic Solvents on Reaction Rates, Journal of Organic Chemistry, (1988), vol. 53, No. 1, pp. 88-92.

Roberto Bovara et al., Enzymatic a/B Inversion of the C-7-Hydroxyl of Steroids, J. Org. Chem., 1993, 499-501, 58, American Chemical Society.

Rudolf Edenharder et al., Characterization of NAD-dependent 3a- and 3B-hydroxysteroid dehydrogenase and of NADP-dependent 7B-hydroxysteroid dehydrogenase from *Peptostreptococcus productus*, Biochimica et Biophysica Acta, 1989, 230-238, 1004, Elsevier Science Publishers B.V.

Rudolf Edenharder et al., Characterization of NADP-dependent 12B-hydroxysteroid dehydrogenase from *Clostridium paraputrificum*, Biochimica et Biophysica Acta, 1988, 362-370, 962, Elsevier Science Publishers B.V.

Rudolf Edenharder et al., Partial Purification and Characterization of an NAD-Dependent 3B-Hydroxysteroid Dehydrogenase from *Clostridium innocuum*, Applied and Environmental Microbiology, Jun. 1989, 1656-1659, vol. 55, No. 6, American Society for Microbiology.

Seiju Hirano et al., Characterization of NADP-Dependent 7B-Hydroxysteroid Dehydrogenases from *Peptostreptococcus productus* and *Eubacterium aerofaciens*, Applied and Environmental Microbiology, May 1982, 1057-1063, vol. 43, No. 5.

Sergio Riva, et al., Enzymatic a/B Inversion of C-3 Hydroxyl of Bile Acids and Study of the Effects of Organic Solvents on Reaction Rates, J. Org. Chem, 1988, 88-92, 53, American Chemical Society.

Tadashi Yoshimoto, Cloning and Sequencing of the 7a-Hydroxysteroid Dehydrogenase Gene from *Escherichia coli* HB101 and Characterization of the Expressed Enzyme, Journal of Bacteriology, Apr. 1991, 2173-2179, vol. 173, No. 7, American Society for Microbiology.

Taiko Akao, Purification and Characterization of 7B-Hydroxysteroid Dehydrogenase from *Ruminococcus* sp. of Human Intestine, J. Biochem, 1987, 613-619, 102, No. 3.

Tea Lanisnik Rizner, Purification and Characterization of 17B-Hydroxysteroid Dehydrogenase from the Filamentous Fungus *Cochliobolus lunatus*, J. Steroid Biochem. Molec. Biol., 1996, 205-214, vol. 59, No. 2.

U.S. Appl. No. 11/910,886, Aug. 3, 2011, Office Action.

U.S. Appl. No. 11/910,886, Jan. 6, 2011, Office Action.

Abokitse, K., "Cloning, sequence analysis, and heterologous expression of the gene encoding a (S)-specific alcohol dehydrogenase from *Rhodococcus erythropolis* DSM 43297," Appl Microbiol Biotechrol (2003) 62:380-386.

Dayhoff, M.O., "A Model of Evolutionary Change in Proteins," Atlas of Protein Sequences and Structure (1978) 5 (3):345-352.

Karlin, S., Methods for assessing the statistical significance of molecular sequence features by using general scoring schemes, Proc. Natl. Acad. Sci. USA, Mar. 1990, vol. 87, pp. 2264-2268.

Lowry, O., "Protein Measurement with Folin Phenol Reagent," J Biol Chem. Nov. 1951; 193(1):265-75.

Peters, J., "A novel NADH-dependent carbonyl reductase with an extremely broad substrate range from *Candida parapsilosis*: Purification and characterization," Enzyme Microb. Technol., Nov. 1993, vol. 15, pp. 950-958.

Peterson, G., "Review of the Folin Phenol Protein Quantitation Method of Lowery, Rosebrough, Farr, and Randall," Analytical Biochemsitry (1979) 100:201-220.

Stampfer, W., "Biocatalytic Asymmetric Hydrogen Transfer Employing *Rhodococcus* rubber DSM 44541," J. Org. Chem. 2003, 68, pp. 402-406.

Tishkov, V., "Pilot Scale Production and Isolation of Recominant NAD+- and NADP+-Specific Formate Dehydrogenases," Biotechnology and Bioengineering, Jul. 20, 1999, vol. 64, No. 2, pp. 187-193.

Xie, S., NAD+-Dependent (S)-Specific Secondary Alcohol Dehydrogenase Involved in Stereoinversion of 3-Pentyn-2-ol Catalyzed by *Nocardia* fusca AKU 2123, Biosci. Biotechnol. Biochem., (1999) 63 (10), pp. 1721-1729.

Oxidoreduction of Cholic Acid and Dehydrocholic Acid, J. Org. Chem., 1986, 2903-2906, vol. 51, No. 15.

Fung, E., R.W. Hyman, D. Rowley, D. Bruno, M. Miranda, M. Fukushima, B.L. Wickes, J. Fu, and R.W. Davis. 2004. *Cryptococcus neoformans* serotype D sequencing. (http://www.ncbi.nlm.nih.gov/entrez/viewer.fcgi?db=protein&id=50257918). Accessed in: Jul. 26, 2007.

OXIDOREDUCTASES FOR THE STEREOSELECTIVE REDUCTION OF KETO COMPOUNDS

CROSS REFERENCE TO RELATED APPLICATIONS

This application is a continuation of copending U.S. patent application Ser. No. 11/996,968, having a 371(c) date of Mar. 19, 2008, which is a national phase of International Patent Application No. PCT/EP2006/007150, filed on Jul. 20, 2006, and which claims the benefit of Austrian Patent Application No. AT 1261/2005, filed Jul. 27, 2005. The disclosures of the foregoing applications are incorporated herein in their entirety.

BACKGROUND

The present invention relates to a process for the enantioselective enzymatic reduction of a keto compound to the corresponding chiral hydroxy compound, wherein the keto compound is reduced with an oxidoreductase. Furthermore, the invention relates to new oxidoreductases for use in the enantioselective reduction of keto compounds to chiral hydroxy compounds.

Optically active hydroxy compounds are valuable chirons with broad applicability for the synthesis of pharmacologically active compounds, aromatic substances, pheromones, agricultural chemicals and enzyme inhibitors. Thereby, an increasing demand for chiral compounds and thus chiral synthesis technologies can be noted particularly in the pharmaceutical industry, since, in the future, racemic compounds will hardly be used as pharmaceutical preparations.

The asymmetric reduction of prochiral keto compounds is a sector of stereoselective catalysis, wherein biocatalysis constitutes a powerful competitive technology versus chemical catalysis. The chemical asymmetric hydrogenation requires the use of highly toxic and environmentally harmful heavy metal catalysts, of extreme and thus energy-intensive reaction conditions as well as large amounts of organic solvents. Furthermore, these methods are often characterized by side reactions and insufficient enantiomeric excesses.

In nature, reductions of prochiral keto compounds to hydroxy compounds and vice versa occur in numerous biochemical pathways, both in the primary metabolism and in the secondary metabolism, in every organism and are catalyzed by different types of secondary alcohol dehydrogenases and oxidoreductases. Normally, these enzymes are cofactor-dependent.

The basic feasibility of using biocatalysts for the reduction of prochiral keto compounds to chiral hydroxy compounds was repeatedly demonstrated in the past on the basis of model systems, wherein both isolated oxidoreductases and various whole-cell biotransformation systems were used for the task. Thereby, the biocatalytic approach turned out to be advantageous essentially with regard to mild reaction conditions, lack of byproducts and often significantly better achievable enantiomeric excesses. The use of isolated enzymes is advantageous over methods involving whole cells with regard to the achievable enantiomeric excess, the formation of degradation products and byproducts as well as with regard to the product isolation. Moreover, the use of whole-cell processes is not possible for every chemical company, since specific equipment and know-how is required therefor.

Recently, it has been possible to demonstrate that the use of isolated oxidoreductases in aqueous/organic two-phase systems with organic solvents is extremely efficient, economical and feasible also at high concentrations (>5%). In the described systems, the keto compound to be reduced, which usually is poorly soluble in water, thereby forms the organic phase together with the organic solvent. Also, the organic solvent itself can partly be dispensed with. In that case, the organic phase is formed from the keto compound to be reduced (DE 10119274, DE 10327454.4, DE 103 37 401.9, DE 103 00 335.5). Coenzyme regeneration is thereby achieved by the concurrent oxidation of secondary alcohols, for which, in most cases, the inexpensive water-miscible 2-propanol is used.

Examples of suitable R- and S-specific oxidoreductases and dehydrogenases of high enantioselectivity are: Carbonyl reductase from *Candida parapsilosis* (CPCR) (U.S. Pat. No. 5,523,223 and U.S. Pat. No. 5,763,236, (Enzyme Microb Technol. 1993 November; 15(11):950-8)) and *Pichia capsulata* (DE10327454.4). Carbonyl reductase from *Rhodococcus erythropolis* (RECR) (U.S. Pat. No. 5,523,223), *Norcardia fusca* (Biosci. Biotechnol. Biochem., 63 (10) (1999), pp. 1721-1729), (Appl Microbiol Biotechnol. 2003 September; 62(4):380-6. Epub 2003 Apr. 26), and *Rhodococcus ruber* (J Org Chem. 2003 Jan. 24; 68(2):402-6.).

R-specific secondary alcohol dehydrogenases from organisms of the genus *Lactobacillus* (*Lactobacillus kefir* (U.S. Pat. No. 5,200,335), *Lactobacillus brevis* (DE 19610984 A1) (Acta Crystallogr D Biol Crystallogr. 2000 December; 56 Pt 12:1696-8), *Lactobacillus minor* (DE10119274) or *Pseudomonas* (U.S. Pat. No. 5,385,833) (Appl Microbiol Biotechnol. 2002 August; 59(4-5):483-7. Epub 2002 Jun. 26., J. Org. Chem. 1992, 57, 1532)

However, the enzymes known today are not nearly sufficient for exploiting the entire market potential of stereoselective reductions of keto compounds. On the one hand, this can be explained by the fact that the individual enzymes have very different properties with respect to substrate spectrum, pH optima as well as temperature and solvent stabilities, which often supplement each other. Therefore, even relatively similar homologous enzymes may exhibit a completely different conversion behaviour with regard to one particular substrate. On the other hand, not nearly all of the enzymes described are cloned and overexpressible to a sufficient extent, which means that these enzymes are not available for industrial use. For exploiting the synthetic potential of the enzymatic asymmetric hydrogenation as extensively as possible, it is therefore necessary to be in possession of a portfolio of different industrially accessible oxidoreductases which is as broad as possible, which oxidoreductases are furthermore suitable for use in aqueous/organic two-phase systems with organic solvents.

SUMMARY

The subject matter of the present invention is now a number of novel, enantioselective R- and S-specific oxidoreductases characterized by good stability in aqueous/organic two-phase systems as well as by good expressibility in *Escherichia coli* (>500 units/g *E. coli* wet biomass), as well as a process for the enantioselective enzymatic reduction of a keto compound to the corresponding chiral hydroxy compound.

DETAILED DESCRIPTION

The oxidoreductases according to the invention are characterized in that they have an amino acid sequence in which:
(a) at least 70% of the amino acids are identical to the amino acids of one of the amino acid sequences SEQ ID No 1, SEQ ID No 6 and SEQ ID No 8, or (b) at least 55% of the amino acids are identical to the amino acids of the amino acid sequence SEQ ID No 2, or
(c) at least 65% of the amino acids are identical to the amino acids of the amino acid sequence SEQ ID No 3, or
(d) at least 75% of the amino acids are identical to the amino acids of the amino acid sequence SEQ ID No 4, or
(e) at least 65% of the amino acids are identical to the amino acids of the amino acid sequence SEQ ID No 5, or
(f) at least 50% of the amino acids are identical to the amino acids of the amino acid sequence SEQ ID No 7.
(g) at least 72% of the amino acids are identical to the amino acids of the amino acid sequence SEQ ID No 129.

The polypeptide according to SEQ ID No 1 can be obtained from yeasts, in particular from yeasts of the genus *Rhodotorula*, in particular from *Rhodotorula mucilaginosa*.

A further subject matter of the invention is a nucleic acid sequence SEQ ID No 9, which codes for the protein having the amino acid sequence SEQ ID No 1.

The oxidoreductase from *Rhodotorula mucilaginosa* reduces, for example, 2-octanone to S2-octanol and preferably oxidizes S-2-octanol out of the two enantiomers of the 2-octanol. The oxidoreductase from *Rhodotorula mucilaginosa* is, for example, a homodimer having a molecular weight determined in the SDS-gel of 30±2 kDa. The pH optimum for the reduction reaction ranges from 7.0 to 8.0 for said oxidoreductase, and the pH optimum for the oxidation reaction is in the range of from 8.5 to 10. The oxidoreductase from *Rhodotorula mucilaginosa* exhibits good temperature and pH stabilities and shows only minor activity losses in the pH range of from 5.5 to 10 and at temperatures of up to 35° C., even with incubation periods of several hours. Furthermore, the oxidoreductase from *Rhodotorula mucilaginosa* exhibits high stability in organic solvents.

Polypeptides according to SEQ ID No 2 or SEQ ID No 8 can be obtained from yeasts, in particular from yeasts of the genera *Pichia, Candida, Pachysolen, Debaromyces* or *Issatschenkia*, in particular from *Pichia farinosa* DSMZ 3316 or *Candida nemodendra* DSMZ 70647. A further subject matter of the invention is a nucleic acid sequence SEQ ID No 10 and a nucleic acid sequence SEQ ID No 16, which code for the amino acid sequences SEQ ID No 2 and SEQ ID No 8, respectively. The oxidoreductase preferably reduces 2-butanone to R-2-butanol and preferably oxidizes R-2-butanol out of the two enantiomers of the 2-butanol.

The oxidoreductase from *Pichia farinosa* exhibits a significantly higher activity towards R-2-butanol and 2-propanol than towards R-2-octanol, in addition, the enzyme exhibits a significantly higher activity towards acetone and 2-butanone than towards 2-octanone.

However, the oxidoreductase from *Candida nemodendra* exhibits a similar activity towards R-2-butanol, 2-propanol and R-2-octanol, in addition, the enzyme also exhibits an approximately similar activity towards 2-octanone.

The oxidoreductase from *Pichia farinosa* is a homodimer having a molecular weight determined in the SDS-gel of 27±2 kDa. The pH optimum for the reduction reaction ranges from 5.0 to 6.0 for said oxidoreductase, and the pH optimum for the oxidation reaction ranges from 7.5 to 10. The oxidoreductase from *Pichia farinosa* exhibits good pH and solvent stabilities and shows only minor activity losses in the pH range of from 5.5 to 10, even with incubation periods of several hours.

The oxidoreductase from *Candida nemodendra* is a homomer having a molecular weight determined in the SDS-gel of 27±2 kDa. The pH optimum for the reduction reaction is at pH 6 for said oxidoreductase, and the pH optimum for the oxidation reaction ranges from 1011. The oxidoreductase from *Candida nemodendra* exhibits good pH and solvent stabilities and shows only minor activity losses in the pH range of from 6.5 to 9.5, even with incubation periods of several hours.

The polypeptides according to SEQ ID No 3 or SEQ ID No 7 can be obtained from yeasts, in particular from yeasts of the genera *Pichia* and *Candida*, in particular from *Pichia stipidis* DSMZ 3651 and *Pichia trehalophila* DSMZ 70391. A further subject matter of the invention is a nucleic acid sequence SEQ ID No 11 and a nucleic acid sequence SEQ ID No 15, which encode polypeptides SEQ ID No 3 and SEQ ID No 7, respectively.

The carbonyl reductases from yeasts of the genera *Pichia* and *Candida*, which have at least 65% identity to the amino acid sequence SEQ ID No 3 or at least 50% identity to the amino acid sequence SEQ ID No 7, preferably reduce 2-octanone to S-2-octanol and preferably oxidize 5-2-octanol out of the two enantiomers of the 2-octanol. They are also particularly suitable for the reduction of 4-haloacetoacetate esters to R-4-halo-3-hydroxybutyric acid esters.

The oxidoreductase from *Pichia stipidis* is a homodimer having a molecular weight determined in the SDS-gel of 36±2 kDa. The pH optimum for the reduction reaction ranges from 5.5 to 6.5 for said oxidoreductase, and the pH optimum for the oxidation reaction ranges from 6.5 to 8.0. The oxidoreductase from *Pichia stipidis* exhibits good pH and solvent stabilities and shows only minor activity losses in the pH range of from 5.5 to 10, even with incubation periods of several hours.

The oxidoreductase from *Pichia trehalophila* is a homomer having a molecular weight determined in the SDS-gel of 36±2 kDa. The pH optimum for the reduction reaction ranges from 7 to 7.5 for said oxidoreductase, and the pH optimum for the oxidation reaction ranges from 7 to 8.

The polypeptide according to SEQ ID No 4 can be obtained from bacteria of the class *Leuconostoc*, in particular from *Leuconostoc carnosum* DSMZ 5576. A further subject matter of the invention is a nucleic acid sequence SEQ ID No 12, which codes for a protein having the amino acid sequence SEQ ID No 4. The polypeptide is particularly suitable for the reduction of 2-octanone to R-2-octanol and for the oxidation of R-2-octanol. It is also very suitable for the reduction of 4-haloacetoacetate esters to S-4-halo-3-hydroxybutyric acid esters.

The oxidoreductase from *Leuconostoc carnosum* is a homodimer having a molecular weight determined in the SDS-gel of 27±2 kDa. The pH optimum for the reduction reaction ranges from 5.0 to 6.0 for said oxidoreductase, and the pH optimum for the oxidation reaction ranges from 6.0-9.0. The oxidoreductase from *Leuconostoc carnosum* exhibits good temperature, pH and solvent stabilities and shows only minor activity losses in the pH range of from 4.5 to 10 and at temperatures of up to 35° C., even with incubation periods of several hours.

The polypeptide according to SEQ ID No 5 can be obtained from bacteria of the class Actinobacteria, in particular from bacteria of the class *Microbacterium*, in particular from *Microbacterium* spec. DSMZ 20028. A further subject matter of the invention is a nucleic acid sequence SEQ ID No 13, which codes for the protein having the amino acid sequence SEQ ID No 5. The polypeptide is very suitable for the reduction of 2-octanone to S-2-octanol and preferably oxidizes 5-2-octanol out of the two enantiomers of the 2-octanol. It is also very suitable for the reduction of 4-haloacetoacetate esters to R-4-halo-3-hydroxybutyric acid esters.

The oxidoreductase from *Microbacterium* spec. DSMZ 20028 is, for example, a homotetramer having a molecular weight determined in the SDS-gel of 35±2 kDa. The pH optimum for the reduction reaction ranges from 6.0 to 7.5 for said oxidoreductase, and the pH optimum for the oxidation reaction ranges from 7.5 to 9.5. The oxidoreductase from *Microbacterium* spec exhibits good temperature, pH and solvent stabilities and shows only minor activity losses in the pH range of from 4.5 to 10 and at temperatures of up to 50° C., even with incubation periods of several hours.

The polypeptide according to SEQ ID No 6 can be obtained from bacteria of the class Actinobacteria, in particular from bacteria of the class *Gordonia*, in particular from *Gordonia rubripertincta* DSMZ 43570. A further subject matter of the invention is a nucleic acid sequence SEQ ID No 14, which codes for the protein having the amino acid sequence SEQ ID No 6. The polypeptide is very suitable for the reduction of 2-octanone to S-2-octanol and preferably oxidizes S-2-octanol out of the two enantiomers of the 2-octanol. It is also very suitable for the reduction of 4-haloacetoacetate esters to R-4-halo-3-hydroxybutyric acid esters.

The oxidoreductase from *Gordonia rubripertincta* DSMZ 43570 is a homomer having a molecular weight determined in the SDS-gel of 41±3 kDa. The pH optimum for the reduction reaction ranges from 4.5 to 5.5 for said oxidoreductase, and the pH optimum for the oxidation reaction ranges from 7.5 to 9.5. The oxidoreductase from *Gordonia rubripertincta* DSMZ 43570 exhibits good temperature, pH and solvent stabilities and shows only minor activity losses in the pH range of from 4.5 to 10 and at temperatures of up to 55° C., even with incubation periods of several hours.

The polypeptide according to SEQ ID No 129 can be obtained from yeasts, in particular from yeasts of the genera *Lodderomyces*, in particular from *Lodderomyces elongisporus* DSMZ 70320. A further subject matter of the invention is a nucleic acid sequence SEQ ID No 130, which codes for the protein having the amino acid sequence SEQ ID No 129. The polypeptide is very suitable for the reduction of 2-octanone to S-2-octanol and preferably oxidizes S-2-octanol out of the two enantiomers of the 2-octanol. It is also very suitable for the reduction of 4-haloacetoacetate esters to R-4-halo-3-hydroxybutyric acid esters.

Furthermore, the invention relates to fusion proteins which are characterized in that they represent oxidoreductases having the amino acid sequences SEQ ID No 1, SEQ ID No 2, SEQ ID No 3, SEQ ID No 4, SEQ ID No 5, SEQ ID No 6, SEQ ID No 7, SEQ ID No 8, SEQ ID No 129 or homologues thereof, which are peptidically linked to a further polypeptide at the N-terminal or carboxy-terminal end. Fusion proteins can, for example, be separated more easily from other proteins or can be recombinantly expressed in larger amounts.

Furthermore, the invention relates to antibodies which specifically bind to oxidoreductases according to SEQ ID No 1, SEQ ID No 2, SEQ ID No 3, SEQ ID No 4, SEQ ID No 5, SEQ ID No 6, SEQ ID No 7, SEQ ID No 8, SEQ ID No 129 or to homologues thereof. The production of these antibodies is performed according to known methods by immunization of appropriate mammals and subsequent recovery of the antibodies. The antibodies can be monoclonal or polyclonal.

Comparisons of amino acid sequences can, for example, be conducted in the internet in protein databases such as, e.g., SWISS-PROT, PIR as well as in DNA databases such as, e.g., EMBL, GenBank etc., using the FASTA-program or the BLAST-program.

In doing so, the optimal alignment is determined by means of the BLAST algorithm (Basic Local Alignment Search Tool) (Altschul et al. 1990, *Proc. Natl. Acd. Sci. USA.* 87: 22642268). As a basis, the PAM30 matrix is used as a scoring matrix for evaluating the sequence similarity. (Dayhoff M O., Schwarz, R. M, Orcutt, B. C. 1978. *"A model of evolutionary change in Proteins"* in *"Atlas of Protein Sequence and structure"* 5(3) M. O. Dayhoff (ed) 345-352, National Biomedical Research foundation).

Furthermore, the invention relates to protein fragments which are characterized in that they represent fragments of the amino acid sequence SEQ ID No 1, with a number of more than 26 amino acids per fragment.

A further subject matter of the invention is a microbial carbonyl dehydrogenase which comprises the amino acid sequence MPATLRLDK (SEQ ID No 17) N-terminally and/or the amino acid sequence QALAAPSNLAPKA (SEQ ID No 18) C-terminally and/or one of the internal partial sequences VEIIKTQVQD (SEQ ID No 19), KVAIITGGAS-GIGL (SEQ ID No 20), SCYVTPEG (SEQ ID No 21), TDFKVDGG (SEQ ID No 22), VMFNNAGIMH (SEQ ID No 23) or VHAREGIRIN (SEQ ID No 24).

Furthermore, the invention relates to protein fragments which are characterized in that they represent fragments of the amino acid sequence SEQ ID No 2, with a number of more than 15 amino acids per fragment.

A further subject matter of the invention is a microbial carbonyl dehydrogenase which comprises the amino acid sequence MAYNFTNKVA (SEQ ID No 25) N-terminally and/or the amino acid sequence TTLLVDGGYTAQ (SEQ ID No 26) C-terminally and/or one of the internal partial sequences EYKEAAFTN (SEQ ID No 27), NKVAIITGGIS-GIGLA (SEQ ID No 28), DVNLNGVFS (SEQ ID No 29), HYCASKGGV (SEQ ID No 30), NCINPGYI (SEQ ID No 31) or LHPMGRLGE (SEQ ID No 32).

Furthermore, the invention relates to protein fragments which are characterized in that they represent fragments of the amino acid sequence SEQ ID No 3, with a number of more than 15 amino acids per fragment.

A further subject matter of the invention is a microbial carbonyl dehydrogenase which comprises the amino acid sequence MSIPATQYGFV (SEQ ID No 33) N-terminally and/or the amino acid sequence SAYEGRVVFKP (SEQ ID No 34) C-terminally and/or one of the internal partial sequences CHSDLHAIY (SEQ ID No 35), GYQQYLLVE (SEQ ID No 36), TFDTCQKYV (SEQ ID No 37), LLTPY-HAM (SEQ ID No 38), LVSKGKVKP (SEQ ID No 39), GAGGLGVNG (SEQ ID No 40), IQIAKAFGAT (SEQ ID No 41) or LGSFWGTS (SEQ ID No 42).

Furthermore, the invention relates to protein fragments which are characterized in that they represent fragments of the amino acid sequence SEQ ID No 4, with a number of more than 18 amino acids per fragment.

A further subject matter of the invention is a microbial carbonyl dehydrogenase which comprises the amino acid sequence MTDRLKNKVA (SEQ ID No 43) N-terminally and/or the amino acid sequence AEFVVDGGYLAQ (SEQ ID No 44) C-terminally and/or one of the internal partial sequences VVITGRRAN (SEQ ID No 45), GGASIINMS (SEQ ID No 46), TQTPMGHI (SEQ ID No 47) or GYIKT-PLVDG (SEQ ID No 48).

Furthermore, the invention relates to protein fragments which are characterized in that they represent fragments of the amino acid sequence SEQ ID No 5, with a number of more than 18 amino acids per fragment.

A further subject matter of the invention is a microbial carbonyl dehydrogenase which comprises the amino acid sequence MKALQYTKIGS (SEQ ID No 49) N-terminally and/or the amino acid sequence LAAGTVRGRAVIVP (SEQ ID No 50) C-terminally and/or one of the internal partial sequences CHSDEFVMSLSE (SEQ ID No 51), VYGP- WGCGRC (SEQ ID No 52), VSLTDAGLTPYHA (SEQ ID No 53), LRAVSAATVIAL (SEQ ID No 54) or DFVGADPTI (SEQ ID No 55).

Likewise, the invention relates to protein fragments which are characterized in that they represent fragments of the amino acid sequence SEQ ID No 6, with a number of more than 26 amino acids per fragment.

A further subject matter of the invention is a microbial carbonyl dehydrogenase which comprises the amino acid sequence MKAIQIIQ (SEQ ID No 56) N-terminally and/or the amino acid sequence DLRGRAVVVP (SEQ ID No 57) C-terminally and/or one of the internal partial sequences TAAGACHSD (SEQ ID No 58), TPYHAIKPSLP (SEQ ID No 59), DFVGLQPT (SEQ ID No 60), VYGAWGCG (SEQ ID No 61), DDARHLVP (SEQ ID No 62), MTLGHEGA (SEQ ID No 63) or GGLGHVGIQLLRHL (SEQ ID No 64).

Furthermore, the invention relates to a cloning vector comprising one or several nucleic acid sequences coding for the carbonyl reductases according to SEQ ID No 1, SEQ ID No 2, SEQ ID No 3, SEQ ID No 4, SEQ ID No 5, SEQ ID No 6, SEQ ID No 7, SEQ ID No 8, SEQ ID No 129 or homologues thereof. Moreover, the invention comprises a cloning vector which, in addition to the carbonyl reductase, includes a suitable enzyme for the regeneration of NAD(P) such as, e.g., formate dehydrogenases, alcohol dehydrogenases or glucose dehydrogenase.

Furthermore, the invention relates to an expression vector located in a bacterial, insect, plant or mammalian cell and comprising a nucleic acid sequence which codes for the carbonyl reductases according to SEQ ID No 1, SEQ ID No 2, SEQ ID No 3, SEQ ID No 4, SEQ ID No 5, SEQ ID No 6, SEQ ID No 7, SEQ ID No 8, SEQ ID No 129 or homologues thereof and is linked in an appropriate way to an expression control sequence. Furthermore, the invention relates to a recombinant host cell which is a bacterial, yeast, insect, plant or mammalian cell and has been transformed or transfected with such an expression vector as well as to a production process for obtaining a carbonyl reductase based on the cultivation of such a recombinant host cell.

Suitable cloning vectors are, for example, ppCR-Script, pCMV-Script, pBluescript (Stratagene), pDrive cloning Vector (Quiagen, Hilden, Germany), pS Blue, pET Blue, pET LIC-vectors (Novagen, Madison, USA) and TA-PCR cloning vectors (Invitrogen, Karlsruhe, Germany).

Suitable expression vectors are, for example, pKK223-3, pTrc99a, pUC, pTZ, pSK, pBluescript, pGEM, pQE, pET, PHUB, pPLc, pKC30, pRM1/pRM9, pTrxFus, pAS1, pGEx, pMAL or pTrx.

Suitable expression control sequences are, for example, trp-lac (tac)-promoter, trp-lac (trc)-promoter, lac-promoter, T7-promoter or XpL-promoter.

The oxidoreductases according to SEQ ID No 1, SEQ ID No 2, SEQ ID No 3, SEQ ID No 4, SEQ ID No 5, SEQ ID No 6, SEQ ID No 7, SEQ ID No 8, SEQ ID No 129 or homologues thereof can be obtained in such a manner that the above-mentioned recombinant E. coli cells are cultivated, the expression of the respective oxidoreductase is induced and subsequently, after about 10 to 18 hours (h), the cells are digested by ultrasonic treatment, by wet grinding with glass beads in a globe mill (Retsch, GmbH, Haan Germany 10 min, 24 Hz) or using a high-pressure homogenizer. The cell extract obtained can either be used directly or purified further. For this purpose, the cell extract is, e.g., centrifuged and the supernatant obtained is subjected to ion exchange chromatography, for example, by ion exchange chromatography on Q-Sepharose Fast Flow® (Pharmacia).

Furthermore, the invention relates to a process for the enantioselective enzymatic reduction of a keto compound to the corresponding chiral hydroxy compound, wherein the keto compound is reduced with an oxidoreductase in the presence of a cofactor, characterized in that an oxidoreductase is used which has an amino acid sequence in which:
(a) at least 70% of the amino acids are identical to the amino acids of one of the amino acid sequences SEQ ID No 1, SEQ ID No 6 and SEQ ID No 8, or
(b) at least 55% of the amino acids are identical to the amino acids of the amino acid sequence SEQ ID No 2, or
(c) at least 65% of the amino acids are identical to the amino acids of the amino acid sequence SEQ ID No 3, or
(d) at least 75% of the amino acids are identical to the amino acids of the amino acid sequence SEQ ID No 4, or
(e) at least 65% of the amino acids are identical to the amino acids of the amino acid sequence SEQ ID No 5, or
(f) at least 50% of the amino acids are identical to the amino acids of the amino acid sequence SEQ ID No 7, or
(g) at least 72% of the amino acids are identical to the amino acids of the amino acid sequence SEQ ID No 129.

A further preferred embodiment of the process according to the invention consists in that the keto compound has the general formula I

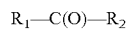

$$R_1\text{—}C(O)\text{—}R_2$$

wherein $R_1$ stands for one of the moieties
1) —$(C_1$-$C_{20})$-alkyl, wherein alkyl is linear-chain or branched,
2) —$(C_2$-$C_{20})$-alkenyl, wherein alkenyl is linear-chain or branched and optionally contains up to four double bonds,
3) —$(C_2$-$C_{20})$-alkynyl, wherein alkynyl is linear-chain or branched and optionally contains up to four triple bonds,
4) —$(C_6$-$C_{14})$-aryl,
5) —$(C_1$-$C_8)$-alkyl-$(C_6$-$C_{14})$-aryl,
6) —$(C_5$-$C_{14})$-heterocycle which is unsubstituted or substituted one, two or three times by —OH, halogen, —$NO_2$ and/or —$NH_2$, or
7) —$(C_3$-$C_7)$-cycloalkyl,
wherein the moieties mentioned above under 1) to 7) are unsubstituted or substituted one, two or three times, independently of each other, by —OH, halogen, —$NO_2$ and/or —$NH_2$, and $R_2$ stands for one of the moieties
8) —$(C_1$-$C_6)$-alkyl, wherein alkyl is linear-chain or branched,
9) —$(C_2$-$C_6)$-alkenyl, wherein alkenyl is linear-chain or branched and optionally contains up to three double bonds,
10) —$(C_2$-$C_6)$-alkynyl, wherein alkynyl is linear-chain or branched and optionally contains two triple bonds, or
11) —$(C_1$-$C_{10})$-alkyl-C(O)—O—$(C_1$-$C_6)$-alkyl, wherein alkyl is linear or branched and is unsubstituted or substituted one, two or three times by —OH, halogen, —$NO_2$ and/or wherein the moieties mentioned above under 8) to 11) are unsubstituted or substituted one, two or three times, independently of each other, by —OH, halogen, —NO2 and/or Furthermore, the invention relates to a process for the enantioselective enzymatic reduction of a keto compound to the corresponding chiral hydroxy compound, wherein the keto compound is reduced with an oxidoreductase in the presence of a cofactor, which process is characterized in that an oxidoreductase is used which:
(a) is encoded by a nucleic acid sequence from the group of SEQ ID No 9, SEQ ID No 10, SEQ ID No 11, SEQ ID No 12, SEQ ID No 13 and SEQ ID No 14, SEQ ID No 15, SEQ ID No 16 and SEQ ID No 130, or which (b) is encoded by a nucleic acid sequence the complementary strand of which hybridizes with one of the nucleic acid sequences mentioned in (a) under highly stringent conditions.

By the term "aryl", aromatic carbon moieties comprising 6 to 14 carbon atoms within the ring are understood. —($C_6$-$C_{14}$)-aryl moieties are, for instance, phenyl, naphthyl, e.g., 1-naphthyl, 2-naphthyl, biphenylyl, e.g., 2-biphenylyl, 3-biphenylyl and 4-biphenylyl, anthryl or fluorenyl. Biphenylyl moieties, naphthyl moieties and in particular phenyl moieties are preferred aryl moieties. By the term "halogen", an element from the family of fluorine, chlorine, bromine or iodine is understood. By the term "—($C_1$-$C_{20}$)-alkyl", a hydrocarbon moiety is understood the carbon chain of which is linear-chain or branched and comprises 1 to 20 carbon atoms, for example, methyl, ethyl, propyl, isopropyl, butyl, tertiary butyl, pentyl, hexyl, heptyl, octyl, nonenyl or decanyl. By the term "—$C_0$-alkyl", a covalent bond is understood.

By the term "—($C_3$-$C_7$)-cycloalkyl", cyclic hydrocarbon moieties such as cyclopropyl, cyclobutyl, cyclopentyl, cyclohexyl or cycloheptyl are understood.

The term "—($C_5$-$C_{14}$)-heterocycle" stands for a monocyclic or bicyclic 5-membered to 14-membered heterocyclic ring which is partially or completely saturated. N, O and S are examples of heteroatoms. Moieties derived from pyrrole, furan, thiophene, imidazole, pyrazole, oxazole, isoxazole, thiazole, isothiazole, tetrazole, 1,2,3,5-oxathiadiazole-2-oxide, triazolone, oxadiazolone, isoxazolone, oxadiazolidinedione, triazoles substituted by F, —CN, —$CF_3$ or —C(O)—O—($C_1$-$C_4$) alkyl, 3-hydroxypyrro-2,4-dione, 5-oxo-1,2,4-thiadiazole, pyridine, pyrazine, pyrimidine, indole, isoindole, indazole, phthalazine, quinoline, isoquinoline, quinoxaline, quinazoline, cinnoline, carboline and benz-anellated, cyclopenta-, cyclohexa- or cyclohepta-anellated derivatives of said heterocycles are examples of the terms "—($C_5$-$C_{14}$)heterocycle". The moieties 2- or 3-pyrrolyl, phenylpyrrolyl such as 4- or 5-phenyl-2-pyrrolyl, 2-furyl, 2-thienyl, 4-imidazolyl, methylimidazolyl, e.g. 1-methyl-2-, -4- or -5-imidazolyl, 1,3-thiazole-2-yl, 2-pyridyl, 3-pyridyl, 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, e.g. 1-methyl, 5-methyl, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl or dihydropyridinyl, pyrrolidinyl, e.g. 2- or 3-(Nmethylpyrrolidinyl), piperazinyl, morpholinyl, thiomorpholinyl, tetrahydrothienyl or benzodioxolanyl are particularly preferred.

Preferred compounds of Formula I are, for example, ethyl-4-chloroacetoacetate, methylacetoacetate, ethyl-8-chloro-6-oxooctanoic acid, ethyl-3-oxovaleriate, 4-hydroxy-2-butanone, ethyl-2-oxovaleriate, ethyl-2-oxo-4-phenylbutyric acid, ethyl pyruvate, ethyl phenyl glyoxylate, 1-phenyl-2-propanone, 2-chloro-1-(3-chlorophenyl)ethane-1-one, acetophenone, 2-octanone, 3-octanone, 2-butanone, 1[3,5-bis(trifluoromethyl)phenyl]ethane-1-one, 2,5-hexanedione, 1,4-dichloro-2-butanone, acetoxyacetone, phenacyl chloride, ethyl-4-bromoacetoacetate, 1,1-dichloroacetone, 1,1,3-trichloroacetone or 1-chloroacetone.

In the process according to the invention, the oxidoreductases can be used either in a completely purified or in a partially purified state or the process can be performed with cells containing the oxidoreductases according to the invention. In doing so, the cells used can be provided in a native, permeabilized or lysed state. The cloned oxidoreductases according to SEQ ID No 1, SEQ ID No 2, SEQ ID No 3, SEQ ID No 4, SEQ ID No 5, SEQ ID No 6, SEQ ID No 7, SEQ ID No 8, SEQ ID No 129 or homologues thereof, respectively, are preferably used.

5.000 to 10 Mio U of oxidoreductase are used per kg of compound of Formula I to be converted (no upper limit). The enzyme unit 1 U corresponds to the enzyme amount which is required for converting 1 μmol of the compound of Formula I per minute (min).

The enzymatic reduction itself proceeds under mild conditions so that the alcohols produced will not react further. The processes according to the invention exhibit a high residence time and an enantiomeric purity of normally more than 95% of the chiral alcohols produced and a high yield, relative to the amount of keto compounds that is employed.

In the process according to the invention, the carbonyl compound is used in an amount of from 3% to 50%, based on the total volume, preferably from 5% to 40%, in particular from 10% to 30%.

Furthermore, a preferred embodiment of the invention is characterized in that the NAD or NADP formed during the reduction is continuously reduced to NADH or NADPH, respectively, with a cosubstrate.

In doing so, primary and secondary alcohols such as ethanol, 2-propanol, 2-butanol, 2-pentanol, 3-pentanol, 4-methyl-2-pentanol, 2-heptanol, 2-octanol or cyclohexanol are preferably used as the cosubstrate.

Said cosubstrates are reacted to the corresponding aldehydes or ketones and NADH or NADPH, respectively, with the aid of an oxidoreductase and NAD or NADP, respectively. This results in a regeneration of the NADH or NADPH, respectively. The proportion of the cosubstrate for the regeneration thereby ranges from 5 to 95% by volume, based on the total volume.

For the regeneration of the cofactor, an additional alcohol dehydrogenase can be added. Suitable NADH-dependent alcohol dehydrogenases are obtainable, for example, from baker's yeast, from *Candida boidinii, Candida parapsilosis* or *Pichia capsulata*. Furthermore, suitable NADPH-dependent alcohol dehydrogenases are present in *Lactobacillus brevis* (DE 196 10 984 A1), *Lactobacillus minor* (DE 101 19 274), *Pseudomonas* (U.S. Pat. No. 5,385,833) or in *Thermoanaerobium brockii*. Suitable cosubstrates for these alcohol dehydrogenases are the already mentioned secondary alcohols such as ethanol, 2-propanol (isopropanol), 2-butanol, 2-pentanol, 4-methyl-2-pentanol, 2-octanol or cyclohexanol.

Furthermore, cofactor regeneration can also be effected, for example, using NAD- or NADP-dependent formate dehydrogenase (Tishkov et al., J. Biotechnol. Bioeng. [1999] 64, 187193, Pilot-scale production and isolation of recombinant NAD and NADP specific Formate dehydrogenase). Suitable cosubstrates of formate dehydrogenase are, for example, salts of formic acid such as ammonium formate, sodium formate or calcium formate. However, the processes according to the invention are preferably carried out without such an additional dehydrogenase, i.e., substrate-coupled coenzyme regeneration takes place.

The aqueous portion of the reaction mixture in which the enzymatic reduction proceeds preferably contains a buffer, e.g., a potassium phosphate, tris/HCl or triethanolamine buffer, having a pH value of from 5 to 10, preferably a pH value of from 6 to 9. In addition, the buffer can comprise ions for stabilizing or activating the enzymes, for example, zinc ions or magnesium ions.

While carrying out the processes according to the invention, the temperature is suitably in the range of from about 10° C. to 70° C., preferably from 20° C. to 40° C.

In a further preferred embodiment of the processes according to the invention, the enzymatic conversion is effected in the presence of an organic solvent which is not miscible with water or miscible with water only to a limited extent. Said solvent is, for example, a symmetric or unsymmetric di(Ci-C6)alkyl ether, a straight-chain or branched alkane or cycloalkane or a water-insoluble secondary alcohol that is simultaneously representing the cosubstrate. The preferred organic solvents are, for example, diethyl ether, tertiary butyl methyl ether, diisopropyl ether, dibutyl ether, butyl acetate, heptane, hexane, 2-octanol, 2-heptanol, 4-methyl-2-pentanol or cyclohexane. The solvent can, at the same time, also serve as a cosubstrate for cofactor regeneration.

If water-insoluble solvents and cosubstrates, respectively, are used, the reaction batch consists of an aqueous and an organic phase. The substrate is distributed between the organic and aqueous phases according to its solubility. The organic phase generally has a proportion of from 5 to 95%, preferably from 10 to 90%, based on the total reaction volume. The two liquid phases are preferably mixed mechanically so that a large surface is produced between them. Also in this embodiment, the NAD or NADP, respectively, formed during the enzymatic reduction can be reduced back to NADH or NADPH, respectively, using a cosubstrate, as described above.

The concentration of the cofactor NADH or NADPH, respectively, in the aqueous phase generally ranges from 0.001 mM to 1 mM, in particular from 0.01 mM to 0.1 mM.

In the processes according to the invention, a stabilizer of the oxidoreductase/dehydrogenase can, in addition, be used. Suitable stabilizers are, for example, glycerol, sorbitol, 1,4-DL-dithiothreitol (DTT) or dimethyl sulfoxide (DMSO).

The process according to the invention is carried out, for example, in a closed reaction vessel made of glass or metal. For this purpose, the components are transferred individually into the reaction vessel and stirred under an atmosphere of, e.g., nitrogen or air. The reaction time ranges from 1 hour to 48 hours, in particular from 2 hours to 24 hours.

Subsequently, the reaction mixture is processed. For this purpose, the aqueous phase is separated, the organic phase is filtered. The aqueous phase can optionally be extracted once more and can be processed further like the organic phase. Thereupon, the solvent is optionally evaporated from the filtered organic phase.

Furthermore, the invention relates to a process for obtaining chiral hydroxy compounds of Formula II, $$R_1—C(OH)—R_2 \quad (II)$$

wherein $R_1$ and $R_2$ are as defined above, which is characterized in that a) a mixture containing the racemic compound of Formula II is incubated in the presence of one of the oxidoreductases of the invention according to SEQ ID No 1, SEQ ID No 2, SEQ ID No 3, SEQ ID No 4, SEQ ID No 5, SEQ ID No 6, SEQ ID No 7, SEQ ID No 8, SEQ ID No 129 or homologues thereof, NAD(P) and water, whereby an enantiomer of the hydroxy compound of Formula II is converted into the corresponding keto compound and NAD(P)H, and b) the remaining enantiomer of the hydroxy compound of Formula II is isolated.

If the carbonyl reductases according to SEQ ID No 1, SEQ ID No 3, SEQ ID No 5, SEQ ID No 6, SEQ ID No 7, SEQ ID No 129 are used, the corresponding chiral R-hydroxy compounds are preferably obtained. If the carbonyl reductases according to SEQ ID No 2, SEQ ID No 4 and SEQ ID No 8 are used, the corresponding chiral S-hydroxy compounds are preferably obtained.

The reaction conditions are basically the same as in the above-mentioned process for the enantiospecific reduction of the keto compound of Formula I. However, instead of an enantioselective reduction of the keto compound of Formula I from the racemic mixture of the compound of Formula II, only one enantiomer of the hydroxy compound of Formula II is oxidized enantioselectively into the corresponding keto compound. Thus, the opposite enantiomer of the hydroxy compound of Formula II remains and can be isolated. Furthermore, instead of the alcohols used as cosubstrates, such as ethanol, 2-propanol (isopropanol), 2-butanol, 2-pentanol or 2-octanol, the corresponding ketones thereof such as acetone are used in the process for the regeneration of the NAD. For example, the acetone and NAD(P)H are converted into NAD and isopropanol by means of the oxidoreductase according to the invention or an additional dehydrogenase.

Preferred embodiments of the invention are illustrated in further detail by means of the following examples.

Example 1

Cultivation of Organisms and Screening for Carbonyl Reductase Activity

For screening, the yeast strains *Rhodotorula mucilaginosa* DSMZ 70825, *Pichia farinosa* DSMZ 3316, *Candida nemodendra* DSMZ 70647, *Pichia stipidis* DSMZ 3651 and *Pichia trehalophila* DSMZ 70391, *Lodderomyces elongisporus* DSMZ 70320 were cultivated in the following medium: yeast extract (3), malt extract (3), peptone (5) and glucose (10) (the numbers in brackets are, in each case, g/l). The medium was sterilized at 121° C. and the yeasts were cultivated without further pH-adjustment at 25° C. and on a shaker at 160 revolutions per minute (rpm).

The strain *Leuconostoc carnosum* DSMZ 5576 was cultivated in the following medium: glucose (20), yeast extract (5), meat extract (10), diammonium hydrogen citrate (2), sodium acetate (5), magnesium sulfate (0.2), manganese sulfate (0.05), dipotassium hydrogen phosphate (2). The medium was sterilized at 121° C. and the organism was cultivated at 30° C. without further pH-adjustment or oxygen supply.

The strain *Microbacterium* spec. DSMZ 20028 was cultivated on a medium of yeast extract (3) and trypticase soy flour (30) at 30° C. and with 160 revolutions per minute (rpm).

The strain *Gordonia rubripertincta* DSMZ 43570 was cultivated on a medium of yeast extract (4), glucose (4), malt extract (10) and CaCO3 (2) at 37° C. and with 160 revolutions per minute (rpm).

Subsequently, 125 mg of cells were resuspended with 800 ill of a digestion buffer (100 mM triethanolamine (TEA), pH=7.0), mixed with 1 g of glass beads and digested for 10 minutes (min) at 4° C. in the globe mill (Retsch). The supernatant (lysate) obtained after 2 min of centrifugation at 12.000 rpm was used in the following activity screening and for determining the enantiomeric excess (ee-value). Different ketones such as 2-butanone, 2-octanone, ethyl-4-chloroacetoacetate, acetophenone or ethyl-2-oxo-4-phenylbutyric acid were used as substrates.

Batch for Activity Screening:

| | |
|---|---|
| 860 ul | 0.1M $KH_2PO_4/K_2PO_4$ pH = 7.0 1 mM $MgCl_2$ |
| 20 ul | NADPH or NADH (10 mM) |
| 20 ul | lysate |
| 100 ul | substrate (100 mM) |

The reaction was pursued for 1 min at 340 nm.
Batch for the Determination of the ee-Value:
20 ul lysate
100 ul NADH or NADPH (50 mM)
60 ul substrate (100 mM)

After 24 hours (h), the batches for ee-determination were extracted, e.g., with chloroform and the enantiomeric excess was determined via gas chromatography (GC). The enantiomeric excess is calculated as follows:

$$ee(\%) = ((R\text{-alcohol} - S\text{-alcohol})/(R\text{-alcohol} + S\text{-alcohol})) \times 100.$$

TABLE 1

| DSMZ No. | Microorganism | Activity in U/g cells host organism | | | |
|---|---|---|---|---|---|
| | | 2-Butanone | | 2-Octanone | |
| | | NADH | NADPH | NADH | NADPH |
| 70825 | Rhodotorula mucilaginosa | <1 | | <1 | |
| 3316 | Pichia farinose | 12 | | <1 | |
| 70647 | Candida nemodendra | 45 | | 12 | |
| 3651 | Pichia stipidis | 10 | | 6.4 | |
| 70391 | Pichia trehalophila | 85 | | 45 | |
| 5576 | Leuconostoc carnosum | — | | | 77 |
| 20028 | Microbacterium spec. | 9 | | 26 | |
| 43570 | Gordonia rubripertincta | 7.7 | | 13 | |
| 70320 | Lodderomyces elogisporus | 40 | | 34 | — |

DSMZ stands for Deutsche Sammlung fur Mikroorganismen and Zellkulturen, Mascheroder Weg 1b, 38124 Braunschweig. Definition of enzyme units: 1 U corresponds to the enzyme amount which is required for converting 1 μmol of substrate per min.

Example 2

Isolation and Purification of NAD(P)H-Dependent Microbial Oxidoreductases

In order to isolate the NAD(P)H-dependent microbial oxidoreductases, the microorganisms were cultivated as described under Example 1. Upon reaching the stationary phase, the cells were harvested and separated from the medium by centrifugation. The enzyme release was effected by wet grinding using glass beads but may also be achieved by other digestion methods. For this purpose, for example, 100 g of wet cell mass were suspended with 400 ml of a digestion buffer (100 mM triethanolamine, 1 mM $MgCl_2$, pH=7.0) and homogenized by means of a French press. The crude extract obtained after centrifugation (7000 rpm) was then purified further via FPLC (fast protein liquid chromatography).

All oxidoreductases according to the invention could be purified by different combinations of ion exchange chromatography, e.g., on Q-Sepharose Fast Flow (Pharmacia) or Uno Q (Biorad, Munich, Germany), hydrophobic interaction chromatography, e.g., on OctylSepharose Fast Flow or Butyl-Sepharose Fast Flow (Pharmacia), ceramic hydroxylapatite chromatography and gel permeation.

Example 2a

Purification of an NADH-Dependent Oxidoreductase from *Pichia farinosa* DSMZ 3316

For protein isolation, the lysate from *Pichia farinosa* DSMZ 3316 obtained after centrifugation was directly applied to a Butyl-Sepharose FF-column equilibrated with 100 mM triethanolamine buffer pH=7.0 1 M $(NH_4)_2SO_4$ and was eluted with a decreasing linear salt gradient. The oxidoreductase-containing fractions were combined and concentrated to an appropriate volume by means of ultrafiltration (exclusion limit 10 kDa).

Subsequently, the concentrated fractions of the oxidoreductase were further purified by Uno Q. For this purpose, the oxidoreductase was directly applied to a Uno Q-column (Biorad) equilibrated with 50 mM potassium phosphate buffer pH=7.0 and was eluted with an increasing linear salt gradient, whereby the oxidoreductase eluted at 0 M NaCl without binding whereas a major part of the impurities was bound and eluted at higher salt concentrations.

The third purification step was performed on a ceramic hydroxylapatite column (Pharmacia), wherein the oxidoreductase was applied to a column equilibrated with 10 mM potassium phosphate buffer, 1 mM $MgCl_2$ pH=6.8 and was eluted with an increasing buffer concentration (400 mM potassium phosphate buffer 1 mM $MgCl_2$ pH=6.8). The oxidoreductase was eluted at 80-100 mM potassium phosphate buffer.

Thereupon, the molecular weight of the purified oxidoreductase obtained was determined via gel permeation (Superdex 200 HR; Pharmacia, 100 mM triethanolamine, pH=7, 0.15 M NaCl). Catalase (232 kDa), aldolase (158 kDa), albumin (69.8 kDa) and ovalbumin (49.4 kDa) were used as molecular weight standards.

The following Table 2 summarizes the results obtained.

TABLE 2

| Purification step | Volume [ml] | Activity [U/ml] 2-butanone | Total activity [U] 2-butanone | Specific activity [U/mg] 2-butanone | Yield |
|---|---|---|---|---|---|
| Crude extract | 70 | 1.3 | 80 | 0.1 | 100% |
| Butyl-Sepharose | 10 | 4.4 | 44 | 1.7 | 55% |
| Uno Q | 1.4 | 17 | 24 | 5 | 30% |
| Hydroxylapatite | 0.7 | 13.5 | 9.5 | 16 | 12% |

The enzyme activity of the oxidoreductase was determined in the test system according to Example 1 (batch activity screening), and the determination of the protein amount was performed according to Lowry et al. *Journal of Biological Chemistry*, 193 (1951): 265-275 or Peterson et al., *Analytical Biochemistry*, 100 (1979): 201-220). The quotient of enzyme activity to protein amount yields the specific activity, wherein the conversion of 1 mmol per min corresponds to 1 unit (U).

Example 2b

Purification of an NADH-Dependent Oxidoreductase from *Microbaceterium* spec. DSMZ 20028

For protein isolation, the lysate from *Microbaceterium* spec. DSMZ 20028 obtained after centrifugation was applied to a Q-Sepharose FF-column equilibrated with 50 mM potassium phosphate buffer pH=7.0 and was eluted with an increasing linear salt gradient. Thereby, the oxidoreductase was eluted at from 0.6 to 0.8 M NaCl. The oxidoreductase-containing fractions were combined and concentrated to an appropriate volume by means of ultrafiltration (exclusion limit 10 kDa).

Subsequently, the concentrated fractions of the oxidoreductase were further purified by Uno Q. For this purpose, the oxidoreductase was directly applied to a UnoQ-column (Biorad) equilibrated with 50 mM potassium phosphate buffer pH=7.0 and was eluted with an increasing linear salt gradient, whereby the oxidoreductase eluted at 0.2-0.25 M NaCl.

The third purification step was performed on a ceramic hydroxylapatite column (Pharmacia), wherein the oxidoreductase from *Microbacterium* spec. DSMZ 20028 was applied to a column equilibrated with 10 mM potassium phosphate buffer, 1 mM MgCl$_2$ pH=6.8 and was eluted with an increasing buffer concentration (400 mM potassium phosphate buffer 1 mM MgCl$_2$ pH=6.8). The oxidoreductase was eluted at 80-100 mM potassium phosphate buffer. Thereupon, the molecular weight of the purified oxidoreductase obtained was determined as described under 2a.

The following Table 3 summarizes the results obtained.

TABLE 3

| Purification step | Volume [ml] | Activity [U/ml] 2-octanone | Total activity [U] 2-octanone | Specific activity [U/mg] 2-octanone | Yield |
|---|---|---|---|---|---|
| Crude extract | 55 | 3.8 | 212 | 0.4 | 100% |
| Q-Sepharose FF | 34 | 4.1 | 139 | 0.56 | 65% |
| Uno Q | 0.8 | 9.3 | 7.5 | 3.8 | 3.5% |
| Hydroxylapatite | 0.5 | 4.2 | 2.1 | 117 | 1% |

Example 3

Determination of the N-Terminal Sequence of an Oxidoreductase According to the Invention After gel permeation in a 10% sodium dodecyl sulfate (SDS) gel, the enzyme preparations according to Example 2 were separated and transferred onto a polyvinylidene difluoride membrane (PVDF-membrane).

The conspicuous band was subjected to N-terminal sequencing via Edman degradation (Procise 492 (PE-Biosystems))

Example 4

General Cloning Strategy of an Enantioselective Alcohol Dehydrogenase Isolated from Yeasts Chromosomal DNA is extracted according to the method described in "Molecular Cloning" by Manniatis & Sambrook. The resulting nucleic acid serves as a template for the polymerase chain reaction (PCR) with degenerate primers. In doing so, 5'-primers are derived from the amino acid sequence (SEQ ID No 66; 72; 80) and 3'-primers are derived from the amino acid sequence (SEQ ID No. 67; 73; 81), involving the genetic code specific for the organism (SEQ ID No. 68; 69; 74; 75; 82; 83).

Amplification is carried out in a PCR buffer [67 mM Tris-HCl (pH 8.3), 16 mM (NH$_4$)$_2$SO$_4$, 115 mM MgCl$_2$, 0.01% Tween 20], 0.2 mM desoxynucleotide triphosphate mix (dNTPs), 40 pMol of each primer and 2.5 U BioTherm Star Polymerase (Genecraft, Ludingshausen, Germany)]. After activation of the BioTherm Star Polymerase (8 min 95° C.) and subsequent 45-50 cycles of a Touch-Down PCR, the reaction is cooled down to 4° C., and the entire PCR batch is applied onto a 1% agarose gel for analysis.

The specific fragment resulting from the polymerase chain reaction is ligated into the TA-cloning vector pCR2.1 (Invitrogen, Karlsruhe, Germany) and sequenced with the primers M13 rev (SEQ ID No 65) and M13 um (SEQ ID No 128) with the aid of an ABI DNA sequencer.

The 5'- and 3'-terminal regions of the gene-coding sequence are determined using the RACE method (rapid amplification of cDNA ends). Based on the nucleic acid sequence of the specific fragment, oligonucleotides for 3'-RACE and 5'-RACE are constructed. Total RNA prepared from the cells serves as a template for the synthesis of the first cDNA strand using the 3'-RACE system (Invitrogen, Karlsruhe, Germany). This is followed by an amplification and a reamplification of the specific cDNA with the aid of 3'-RACE oligonucleotides (SEQ ID No. 76; 77; 84; 85). Subsequently, the batch is applied onto a 1% agarose gel for analysis. The specific fragment carrying the missing 3'-flanking sequence information is isolated, ligated into a TA-cloning vector pCR2.1 and sequenced.

The coding and non-coding 5'-terminal sequences are determined using the 5'-RACE system (Invitrogen). For this purpose, mRNA from the total RNA obtained previously is enriched with the aid of Oligo dT-cellulose (NEB, Beverly, USA) and employed for the synthesis of the first cDNA strand with the gene-specific oligonucleotides (SEQ ID No. 70; 71; 78; 79; 86; 87). The subsequent amplification and reamplification of the specific cDNA results in a fragment which is ligated into a pCR2.1 TA-cloning vector (Invitrogen) for analysis. The plasmid containing the fragment is analyzed with the aid of an ABI DNA sequencer. Thus, the missing sequence information about the 5'-end of the gene is obtained.

| Protein | *Rhodotorulla mucilaginosa* | *Pichia farinosa* | *Pichia stipitis* |
|---|---|---|---|
| Partially sequenced peptides | VATAVETFGR (SEQ ID No 66) FGEAVEQAR (SEQ ID No 67) | LLTQTLALEQAK (SEQ ID No 72) YNFTNKVAIITGGI (SEQ ID No 73) | ADQVLLK (SEQ ID No 80) ISFNLGDLALR (SEQ ID No 81) |
| Primer for Touch-Down PCR | CCRAAYTCVACVGCVGTSGC (SEQ ID No 68) GCCTGYTCGACVGCYTCRCC (SEQ ID No 69) | YTGYTCYAANGCYAADGTYTG (SEQ ID No 74) CHAAYAARGTNGCHATHATYA CHGG (SEQ ID No 75) | GCYGAYCARGTNTTRTTRA AR (SEQ ID No 82) CTYAARGCYAARTCDCCYA AR (SEQ ID No 83) |
| Primer for 3'-RACE | | CAACGTTCTGAAGAGATGACT TA TG (SEQ ID No 76) GGTGGAGTGAAGTTATTGAC (SEQ ID No 77) | CTACCATGCCATGAGATTA G (SEQ ID No 84) GCTGTAGACGTCGCTAAGA G (SEQ ID No 85) |
| Primer for 5'-RACE | CTCCGAGGTGTTGAGCGCAT TG (SEQ ID No 70) GACGAGGTTCTTGATGTCGT | GCCATTCTTAGCCTGTTCGAGA G (SEQ ID No 78) GTCATCTCTTCAGAACGTTGAT | GATTCTCAAGGCTAAGTCA C (SEQ ID No 86) GATCTAACACCAGCTAATC |

-continued

| Protein | Rhodotorulla mucilaginosa | Pichia farinosa | Pichia stipitis |
|---|---|---|---|
| | CCTCC (SEQ ID No 71) | CTT (SEQ ID No 79) CCAAAGGAGCTTATAGCAGTC T (SEQ ID No 88) | T (SEQ ID No 87) |

Based on the sequence coding for the full-length gene (SEQ ID No. 9; 10; 11), specific primers for subsequent cloning of said DNA section into an appropriate expression system are constructed. For this purpose, for example, 5'-primers with a recognition sequence for Nde I or with a recognition sequence for Sph I, or for BamHI, respectively, and 3'-primers with a recognition sequence for Hind III are modified (SEQ ID No. 89; 90; 91; 92; 93; 94; 95; 96).

In the subsequent PCR, chromosomal DNA serves as the template. The DNA section coding for the respective oxidoreductase is amplified with the aid of *Platinum pfx* Polymerase (Invitrogen). After purification over 1% agarose gel, the resulting PCR product is treated with appropriate DNA endonucleases and ligated into the backbone of the pET21a vector (Novagen, Madison, USA) or into the backbone of the pQE70 vector (Qiagen, Hilden, Germany), respectively, which backbone has been treated with the same endonucleases.

After sequencing, the expression construct formed is taken into the expression strain BL21 Star (Invitrogen) or RB791 (*E. coli* genetic stock, Yale, USA), respectively.

4a. Cloning of an Enantioselective Oxidoreductase from the Yeast *Pichia farinosa*

For cloning the oxidoreductase from *Pichia* farinosa, chromosomal DNA was, for example, extracted from the fresh cells of *Pichia Farinosa* according to the method described in "Molecular cloning" by Manniatis & Sambrook. The resulting nucleic acid served as a template for a Touch-Down PCR with oligonucleotides SEQ ID No. 74; 75. After 8 minutes of activating the Biotherm Star Polymerase in a PCR Cycler (BioRad, Hercules, USA), the following 30 temperature cycles were programmed for an identification of the specific DNA fragment:

| | |
|---|---|
| 94° C. | 45 sec |
| 60° C.-0.5° C./cycle | 45 sec |
| 68° C. | 2 min |

Subsequently, the amplification signal was increased by another 20 cycles

| | |
|---|---|
| 94° C. | 40 sec |
| 52° C. | 40 sec |
| 72° C. | 1 min. |

After the fractionation of the entire reaction batch in 1% agarose gel, a specific fragment having a size of 550 by was detected. Said fragment was eluted from the gel and ligated into the pCR2.1 TA-vector (Invitrogen, Karlsruhe, Germany). The plasmid pCR2.1-PF550 formed was subjected to sequencing.

A sequence analysis of the gene fragment having a length of 550 by showed an open reading frame of 174 amino acid residues, in which the two sequence fragments of the N-terminus and of the internal peptide could also be found.

Based on the nucleotide sequence of the fragment having a length of 521 bp, oligonucleotides for a 3'-RACE (SEQ ID No 76; 77) and a 5'-RACE (SEQ ID No 78; 79; 88) were constructed. For the cDNA synthesis reaction, the total RNA from the cells of *Pichia farinosa* was prepared as follows.

600 mg of fresh cells were resuspended in 2.5 ml of ice-cold LETS buffer. 5 ml (about 20 g) of glass beads washed in nitric acid and equilibrated with 3 ml phenol (pH 7.0) were added to said cell suspension. The entire batch was then vortexed in each case for 30 sec, in total for 10 min, and was cooled on ice for 30 sec. Subsequently, 5 ml of an ice-cold LETS buffer were added and thoroughly vortexed once again. Said cell suspension was centrifuged at 11000 g and at 4° C. for 5 min. The aqueous phase was recovered and extracted twice with an equal volume of phenol:chloroform:isoamyl alcohol (24:24:1). This was subsequently followed by the extraction with chloroform. After the final extraction, the total RNA was precipitated at −20° C. for 4 h by adding 1/10 vol. of 5 M $LiCl_2$. The synthesis of the first cDNA strand was carried out using the 3'RACE system (Invitrogen, Karlsruhe, Germany). Subsequently, the specific cDNA was amplified with the oligonucleotides SEQ ID No 76 and AUAP (Invitrogen, Karlsruhe, Germany) in the reaction: 67 mM Tris-HCl (pH 8.3), 16 mM (NH4)2504, 115 mM $MgCl_2$, 0.01% Tween 20], 0.2 mM desoxynucleotide triphosphate mix (dNTPs), 10 pMol of each primer and 2.5 U BioTherm Star Polymerase (Genecraft, Lndingshausen, Germany) and with the following 30 temperature cycles: 94° C. 40 sec, 55° C. 40 sec, 72° C. 1 min.

The PCR signal was increased via a nested PCR with primer SEQ ID No 77 and primer UAP (Invitrogen, Karlsruhe, Germany) with 30 temperature cycles: 94° C. 40 sec, 55° C. 40 sec, 72° C. 50 sec. The result was a specific DNA fragment having a size of approximately 400 bp, which was ligated after isolation into the vector pCR2.1 (Invitrogen) from the 1% agarose gel. The sequence analysis of the DNA section having a length of 382 by yielded sequence information about the 3'-extension up to the stop codon and the poly-A loop of the cDNA coding for the oxidoreductase from *Pichia Farinosa*.

For the 5'RACE reaction, 5 fig of total RNA prepared from the cells of *Pichia farinosa* were used. The synthesis of gene-specific cDNA was performed using the 5'RACE system (Invitrogen, Karlsruhe, Germany) and the oligonucleotide SEQ ID No 78. The resulting gene-specific cDNA was subjected to a homopolymeric dCTP addition reaction. This was subsequently followed by an amplification of the cDNA in a PCR [67 mM Tris-HCl (pH 8.3), 16 mM $(NH_4)2504$, 115 mM $MgCl_2$, 0.01% Tween 20], 0.2 mM desoxynucleotide triphosphate mix (dNTPs), 20 pMol primer SEQ ID No 79 and primer AAP (Invitrogen), 2.5 U BioTherm Star Polymerase (Genecraft, Lndingshausen, Germany) and with the following 35 temperature cycles: 94° C. 45 sec, 54° C. 45 sec, 72° C. 1 min 30 sec. The PCR signal was increased via a nested PCR with primer SEQ ID No 88 and primer UAP (Invitrogen, Karlsruhe, Germany) with 30 temperature cycles: 94° C. 40 sec, 55° C. 40 sec, 72° C. 1 min. The result was a specific DNA fragment having a size of approximately 350 bp, which was ligated after elution into the vector pCR2.1 (Invitrogen) from the 1% agarose gel. The sequence analysis of the DNA segment having a length of 352 by yielded sequence information about the 5'-end of the cDNA coding for the alcohol dehydrogenase/reductase.

Thus, the DNA segment coding for the protein has a total length of 765 by (SEQ ID No 10) and an open reading frame of 254 amino acids (SEQ ID No 2). Chromosomal DNA of the Pichia farinosa cells was used as a template for the generation of the full-length DNA in a polymerase chain reaction [10 mM Tris-HCl, (pH 8.0); 50 mM KCl; 10 mM MgSO4; 0.2 mM dNTP Mix; 20 pMol Primer SEQ ID No 91 or, respectively, 20 pMol Primer SEQ ID No 92, 20 pMol Primer SEQ ID No 93 and 2 U Platinum pfx Polymerase (Invitrogen)] and with temperature cycles:

| Cycle 1 | 94° C., 2 min |
|---|---|
| Cycle 2 × 30 | 94° C., 15 sec |
| | 56° C., 20 sec |
| | 68° C., 1 min 15 sec. |

After purification over 1% agarose gel, the resulting PCR product was treated with Nde I and Hind III, or with Sph I and Hind III, respectively, and was ligated into the backbone of the vector pET21a (Novagen, Madison, USA) or pQE70 (Qiagen, Hilden, Germany), respectively, which backbone had been treated with the same endonucleases. After the transformation of 2 μl of the ligation batch into E. coli Top 10F' cells, plasmid DNAs of ampicillin-resistant colonies were checked for the correctness of the ligation that had been performed by means of a restriction analysis with the endonucleases Nde I or Sph I and Hind III, respectively. The DNA of the vectors positive for the insert was transformed into the expression strain BL21 Star (Invitrogen) and RB791 (E. coli genetic Stock, Yale, USA), respectively.

Example 5

General Cloning Strategy of an Enantioselective Oxidoreductase Isolated from Bacteria Genomic DNA is extracted according to the method described in "Molecular cloning" by Manniatis & Sambrook. The resulting nucleic acid serves as a template for the polymerase chain reaction (PCR) with degenerate primers. In doing so, 5'-primers are derived from the amino acid sequence (SEQ ID No 104; 112) and 3'-primers are derived from the amino acid sequence (SEQ ID No 105; 113), involving the genetic code specific for the organism (SEQ ID No 106; 107; 114; 115).

Amplification is carried out in a PCR buffer [67 mM Tris-HCl (pH 8.3), 16 mM $(NH_4)_2SO_4$, 115 mM $MgCl_2$, 0.01% Tween 20], 0.2 mM desoxynucleotide triphosphate mix (dNTPs), 40 pMol of each primer and 2.5 U BioTherm Star Polymerase (Genecraft, Ludingshausen, Germany)]. After activation of the BioTherm Star Polymerase (8 min 95° C.) and subsequent 45-50 cycles of a Touch-Down PCR, the reaction is cooled down to 4° C., and the entire PCR batch is applied onto a 1% agarose gel for analysis.

The specific fragment resulting from the polymerase chain reaction is ligated into the TA-cloning vector pCR2.1 (Invitrogen, Karlsruhe, Germany) and sequenced with the primers M13 rev (SEQ ID No 65) and M13 um (SEQ ID No 128) with the aid of an ABI DNA sequencer.

The 5'- and 3'-terminal regions of the gene-coding sequence are determined using the inverse polymerase chain reaction method (iPCR). Based on the nucleic acid sequence of the specific internal fragment, oligonucleotides SEQ ID No 100; 101; 102; 103; 108; 109; 110; 111; 116; 117; 118; 119 are constructed. Genomic DNA is digested by means of a restriction endonuclease and used in a religation so that smaller DNA sections can circulate. Said religation mixture is then used as a template for an iPCR and primers SEQ ID No 100; 102; 108; 110; 116; 118. The PCR signal is increased by a subsequent nested PCR with primers SEQ ID No 101; 103; 109; 111; 117; 119. The resulting specific fragment is ligated after elution into the vector pCR2.1 (Invitrogen) from the 1% agarose gel.

Thus, the sequence analysis of the vector pCR2.1 containing the fragment yields the missing sequence information about 3'- and 5'-coding regions of the alcohol dehydrogenase/reductase gene.

| Protein | Leuconostoc carnosum | Microbacterium sp. | Gordonia rubropertincta |
|---|---|---|---|
| Partially sequenced peptides | NIEETTYEDWK (SEQIDNo 97) | MKALQYTKIGSHPE (SEQIDNo 104) AYEALAAGTVV (SEQIDNo 105) | MKAIQIIQPG (SEQIDNo 112) VGFFTQPYEVSVR (SEQIDNo 113) |
| Primer for Touch-Down PCR | GACAGAWMGWTTNAARGG WAARGTHGC (SEQIDNo 98) GCBGTRTAWCCNCCRTCDAC DACRAAYTC (SEQIDNo 99) | CTSCARTACACVAAGATCGG (SEQIDNo 106) GCBGCSAGBGCYTCRTABGC (SEQIDNo 107) | ATGAARGCNATYCARATY ATYCARCC (SEQIDNo 114) CYTCRTANGGYTGNGTRAA RAA (SEQIDNo 115) |

| Primer for iPCR | CTAAGCCAATACCAAGTGTA CCA (SEQIDNo 100) GAACAAATCGTGCTACTGAT TCATCAC (SEQIDNo 101) GAAGAAGCCCAATCACAAAG AACTC (SEQIDNo 102) GGCAGTCTATTTAGCTAGTG AAG (SEQIDNo 103) | TCCTCGCTGAGGCTCATCAC (SEQIDNo 108) GCTTCTCGATCTCGACGACTTC (SEQIDNo 109) GCGCAGCGAACTGATCGAG (SEQIDNo 110) GATCCAGCGCTACTCACTCGAC (SEQIDNo 111) | GAGGACGAAGTCGTCCGA ATG (SEQIDNo 116) GCCGTCACCTTCAGCAACA CC (SEQIDNo 117) CTCGACGTGAGCGACGAC AAG (SEQIDNo 118) GCAAGATCACCGGCAACG ATG (SEQIDNo 119) |
|---|---|---|---|

Based on the sequence coding for the full-length gene (SEQ ID No. 12; 13; 14), specific primers for subsequent cloning of said DNA section into an appropriate expression system are constructed. In doing so, 5'-primers are modified with a recognition sequence for Nde I or with a recognition sequence for Sph I, or for BamHI, respectively, and 3'-primers with a recognition sequence for Hind III (SEQ ID No. 120; 121; 122; 123; 124; 125; 126; 127).

The amplification of the full-length DNA from genomic DNA, which full-length DNA codes for the protein, with subsequent restriction and ligation into the expression vector is performed as described in Example 3. The expression strain BL21 Star (Invitrogen) or RB791 (*E. coli* genetic stock, Yale, USA), respectively, is transformed with the expression construct formed.

5a Cloning of an Enantioselective Alcohol Dehydrogenase/Reductase from the Microorganism *Microbacterium* Sp.

For cloning the oxidoreductase from *Microbacterium* sp., genomic DNA was, for example, extracted from the fresh cells of *Microbacterium* sp. according to the method described in "Molecular cloning" by Manniatis & Sambrook. The resulting nucleic acid served as a template for a PCR with 30 pMol each of oligonucleotides SEQ ID No. 106; 107. After 10 minutes of activating the Biotherm Star Polymerase in a PCR Cycler (BioRad, Hercules, USA), the following 30 temperature cycles were programmed for an identification of the specific DNA fragment:

| | |
|---|---|
| 94° C. | 50 sec |
| 60° C. | 1 min |
| 72° C. | 1 min |

After the fractionation of the entire reaction batch in 1% agarose gel, a specific fragment having a size of approximately 1000 by was detected. Said fragment was eluted from the gel and ligated into the pCR2.1 TA-vector (Invitrogen, Karlsruhe, Germany). The plasmid pCR2.1-Ms1000 formed was subjected to sequencing.

A sequence analysis of the gene fragment having a length of 1002 by showed an open reading frame of 334 amino acid residues, in which the two sequence fragments of the N-terminus and of the internal peptide could also be found.

Based on the nucleotide sequence of the fragment having a length of 1002 bp, oligonucleotides (SEQ ID No 108; 109; 110; 111) for an inverse PCR (iPCR) were constructed.

Genomic DNA (2.5 µg) from the cells of *Microbacterium* sp. was treated in a 50 µl batch with 20 U restriction endonuclease Sac I for 25 min. After the phenol:chloroform:isoamyl alcohol (25:24:1) extraction of the entire batch and after precipitation with 1/10 vol. of 3M Na-acetate (pH 5.2) and 2.5 vol. of ethanol, the DNA thus digested was transferred into 25 ill H2O. 5 µl (200 ng) thereof were used in a religation reaction in a total volume of 40 µl and 2 U of T4 ligase (Fermentas). The religated genomic DNA (211=20 ng) was then used in an iPCR [67 mM Tris-HCl (pH 8.3), 16 mM (NH4)2SO4, 115 mM MgCl2, 0.01% Tween 20], 0.2 mM desoxynucleotide triphosphate mix (dNTPs), 30 pMol of each primer (SEQ IDNo 108; 110) with 2.5 U BioTherm Star Polymerase (Genecraft, Ludingshausen, Germany)]. The amplification was conducted with the following cycles:

| | |
|---|---|
| Cycle 1 | 95° C., 10 min |
| Cycle 2 × 30 | 95° C., 1 min |
| | 56° C., 1 min |
| | 72° C., 2 min |

The amplification signal was increased in a nested PCR with the oligonucleotides SEQ ID No 109 and SEQ ID No 111.

Subsequently, the amplification reaction was cooled down to 4° C. and applied as a whole onto a 1% agarose gel. The result was a specific fragment having a size of approximately 1000 bp. After the elution from the gel, the fragment was ligated into the pCR2.1 vector (Invitrogen, Karlsruhe, Germany).

The sequence analysis of the plasmid containing the fragment yielded information about the 5'- and 3'-flanking sequences. Thus, the DNA segment coding for the protein has a total length of 1044 by ending in a stop codon (SEQ ID No 13) and exhibits an open reading frame of 347 amino acids (SEQ ID No 5).

Genomic DNA of *Microbacterium* sp. cells was used as a template for the generation of the full-length DNA coding for the protein in a polymerase chain reaction using the GC-Rich PCR system (Roche, Mannheim, Germany) and 30 pMol oligonucleotides SEQ ID No 123 or SEQ ID No 124, respectively, with 30 pMol oligonucleotide SEQ ID No 125 and temperature cycles:

| | |
|---|---|
| Cycle 1 | 95° C., 3 min |
| Cycle 2 × 30 | 95° C., 30 sec |
| | 59° C., 30 sec 72° C., 45 sec. |

After purification over 1% agarose gel, the resulting PCR product was treated with Nde I and Hind III, or with Sph I and Hind III, respectively, and was ligated into the backbone of the vector pET21a (Novagen, Madison, USA) or pQE32 (Qiagen, Hilden, Germany), respectively, which backbone had been treated with the same endonucleases. After the transformation of 2 nl of the ligation batch into *E. coli* Top 10F' cells, plasmid DNAs of ampicillin-resistant colonies were checked for the correctness of the ligation that had been performed by means of a restriction analysis with the endonucleases Nde I or Sph I and Hind III, respectively. The DNA of the vectors positive for the insert was transformed into the expression strain BL21 Star (Invitrogen) and RB791 (*E. coli* genetic Stock, Yale, USA), respectively.

Example 6

Expression of Recombinant Alcohol Dehydrogenases/Reductases in *E. Coli*

The *Escherichia coli* strains BL21 Star (Invitrogen, Karlsruhe, Germany) and RB791 (*E. coli* genetic stock, Yale, USA), respectively, which had been transformed with the expression construct, were cultivated in 200 ml of LB-medium (1% tryptone, 0.5% yeast extract, 1% NaCl) with ampicillin (50 µg/ml) and carbenicillin (50 µg/ml), respectively, until an optical density of 0.5 measured at 550 nm was achieved. The expression of recombinant protein was induced by the addition of isopropyl thiogalactoside (IPTG) at a concentration of 0.1 mM. After 8 hours or after 16 hours, respectively, of induction at 25° C. and 220 rpm, the cells were harvested and frozen at −20° C. For the activity test, 10 mg of cells were mixed with 500 nl of 100 mM TEA buffer pH 7.0 and 500 nl of glass beads and were digested for 10 min using a globe mill. The lysate obtained was then used for the respective measurements in a diluted state. The activity test was composed as follows: 870 ill of 100 mM TEA buffer pH 7.0, 160 µg NAD(P)H, 10 ill diluted cell lysate. The reaction was started with the addition of 100 ill of a 100 mM substrate solution to the reaction mixture.

|  | Expression vector | Expression strain | Substrate | Activity U/g |
|---|---|---|---|---|
| SEQ ID No 1 | pET2la | BL21 Star | acetophenone | 4700 U/g |
| SEQ ID No 2 | pET2la | BL21 Star | 2-butanone | 1900 U/g |
| SEQ ID No 3 | pQE70 | RB791 | CLAEE | 5220 U/g |
| SEQ ID No 4 | pET2la | BL21 Star | CLAEE | 8300 U/g |
| SEQ ID No 5 | pET2la | BL21 Star | 2-octanone | 8000 U/g |
| SEQ ID No 6 | pQE70 | RB791 | 2-octanone | 1600 U/g |
| SEQ ID No 7 | pET2la | BL21 Star |  |  |
| SEQ ID No 8 | pET2la | BL21 Star | CLAEE | 7000 U/g |

Example 7

Characterization of the Recombinant Oxidoreductases

7a: pH-Optimum

The buffers listed in Table 4 were produced. The concentration of the respective buffer components in each case amounted to 50 mM.

TABLE 4

| pH-value | Buffer system |
|---|---|
| 4 | Na-acetate/acetic acid |
| 4.5 | Na-acetate/acetic acid |
| 5 | Na-acetate/acetic acid |
| 5.5 | $KH_2PO_4/K_2PO_4$ |
| 6 | $KH_2PO_4/K_2PO_4$ |
| 6.5 | $KH_2PO_4/K_2PO_4$ |
| 7 | $KH_2PO_4/K_2PO_4$ |
| 7.5 | $KH_2PO_4/K_2PO_4$ |
| 8 | $KH_2PO_4/K_2PO_4$ |
| 8.5 | $KH_2PO_4/K_2PO_4$ |
| 9 | glycine/NaOH |
| 9.5 | glycine/NaOH |
| 10 | glycine/NaOH |
| 11 | glycine/NaOH |

Measuring Batch (30° C.)-pH Optimum Reduction:

| 870 ul | of the buffer systems each mentioned in Table 3 |
| 20 µl | of NAD(P)H 10 mM |
| 10 µl | of a diluted enzyme |

Incubation was performed for about 2 to 3 min, subsequently
100 ul of a substrate solution (100 mM) were added.

Depending on the oxidoreductase, 2-butanone or 2-octanone was used as the substrate. The reaction was pursued for 1 min at 340 nm. In order to determine the pH-optimum, the enzymatic reaction in the respective buffer listed in Table 4 was analyzed. In order to determine the pH-optimum for the oxidation reaction, NAD(P) was used as the cofactor and 2-propanol or 2-octanol was used as the substrate.

The results for the oxidoreductases according to the invention are compiled in Table 5.

TABLE 5

| DSMZ No. | Microorganism | pH-opt red | pH-opt ox |
|---|---|---|---|
| 70825 | Rhodotorula mucilaginosa | 7-8 | 8.0-9.5 |
| 3316 | Pichia farinosa | 5-6 | 7-11 |
| 70647 | Candida nemodendra | 6 | 10-11 |
| 3651 | Pichia stipidis | 5.5-6.5 | 6.5-7.5 |
| 70391 | Pichia trehalophila | 7-7.5 | 7-8 |
| 5576 | Leuconostoc carnosum | 5.0-6 | 6.5-9.5 |
| 20028 | Microbacterium spec. | 6.5-7.5 | 7.5-8.5 |
| 43570 | Gordonia rubripertincta | 5 | 7.5-9.5 |

7b: pH Stability

The determination of the activity of the recombinant oxidoreductases was examined by storing them in the buffer systems mentioned in Table 4. For this purpose, the different buffers (50 mM) were prepared in the range of from pH 4 to 11, and the oxidoreductase produced according to Example 4 was diluted therewith. After 30, 60 and 120 minutes of incubation, 10 pi were taken from the batch and used in the activity test according to Example 1.

The initial value is thereby the measured value which was obtained immediately after the dilution (1:20) of the enzyme in a potassium phosphate buffer 50 mM pH=7.0. Under the given conditions, said value corresponded to an extinction change of approx. 0.70/min and was set as a 100% value, and all subsequent measured values were put in relation to this value.

In Table 6, the pH ranges in which the enzymes exhibited no less than 50% of the initial activity with an incubation lasting for 120 min are compiled for the oxidoreductases according to the invention.

TABLE 6

| DSMZ No. | Microorganism | pH-range stability |
|---|---|---|
| 70825 | Rhodotorula mucilaginosa | 5.5-9.5 |
| 3316 | Pichia farinosa | 5.5-10.0 |
| 70647 | Candida nemodendra | 6.5-9.5 |
| 3651 | Pichia stipidis | 6.0-7.0 |
| 70391 | Pichia trehalophila | 6.0-8.0 |
| 5576 | Leuconostoc carnosum | 4.5-9.5 |
| 20028 | Microbacterium spec. | 5.0-9.5 |
| 43570 | Gordonia rubripertincta | 4.5-10 |

7c: Temperature Optimum

In order to determine the optimum test temperature, the enzyme activity for the oxidoreductases according to the invention was measured in the standard measuring batch in a temperature range of from 15° C. to 70° C.

The temperature optima determined are compiled in Table 7:

TABLE 7

| DSMZ No. | Microorganism | Topt |
|---|---|---|
| 70825 | Rhodotorula mucilaginosa | 50° C. |
| 3316 | Pichia farinosa | 40° C. |
| 70647 | Candida nemodendra | 65° C. |
| 3651 | Pichia stipidis | 40° C. |
| 70391 | Pichia trehalophila | n.b. |
| 5576 | Leuconostoc carnosum | 60° C. |
| 20028 | Microbacterium spec. | 60° C. |
| 43570 | Gordonia rubripertincta | 45-55° C. |

7d: Temperature Stability

In an analogous manner as described under Example 5c, the temperature stability was determined for the range of from 15° C. to 70° C. For this purpose, a dilution of the oxidoreductases according to the invention was in each case incubated at the respective temperature for 60 min and 180 min and was subsequently measured at 30° C. with the above-mentioned test batch. In Table 8, the temperature ranges in which the enzymes exhibited no less than 50% of the initial activity with an incubation lasting for 120 min are compiled for the oxidoreductases according to the invention.

TABLE 8

| DSMZ No. | Microorganism | Temperature stability |
| --- | --- | --- |
| 70825 | Rhodotorula mucilaginosa | 15-35° C. |
| 3316 | Pichia farinose | 15-25° C. |
| 70647 | Candida nemodendra | 15-35° C. |
| 3651 | Pichia stipidis | 15-35° C. |
| 70391 | Pichia trehalophila | 15-35° C. |
| 5576 | Leuconostoc carnosum | 15-35° C. |
| 20028 | Microbacterium spec. | 15-60° C. |
| 43570 | Gordonia rubripertincta | 15-55° C. |

7e: Substrate Spectrum

The substrate spectrum of the oxidoreductases according to the invention was determined by measuring the enzyme activity for reduction and oxidation with a number of ketones and alcohols. For this purpose, the standard measuring batch according to Example 1 was used with different substrates.

The activity with methyl acetoacetate was set to 100% for all enzymes and all the other substrates were put in relation thereto.

TABLE 9

Substrate spectra reduction

| Substrate | Rhodotorula mucilaginosa SEQ ID NO 1 | Pichia farinosa SEQ ID NO 2 | Pichia stipidis SEQ ID NO 3 | Leuconostoc carnosum SEQ ID NO 4 | Microbacterium spec. SEQ ID NO 5 | Gordonia rubripertincta SEQ ID NO 6 |
| --- | --- | --- | --- | --- | --- | --- |
| 1-Phenyl-2-propanone | 66% | 10% | 30% | 13% | 80% | 82% |
| Phenacyl chloride | 36% | 130% | 9% | 37% | <2% | 7% |
| Acetophenone | 12% | 195% | 32% | 28% | 52% | 23% |
| Acetonaphthone | n.b. | 25% | 84% | n.b. | 125% | 68% |
| Butyrophenone | 0% | 0% | 0% | 0% | 0% | 0% |
| 2-Octanone | 71% | 20% | 27% | 28% | 227% | 75% |
| 3-Octanone | 29% | 10% | 40% | 18% | 47% | 52% |
| 2-Butanone | 190% | 65% | 49% | 36% | 4% | 14% |
| Ethyl-2-oxovaleriate | 4% | 85% | 60% | 25% | <2% | 23% |
| Ethyl-2-oxo-4-phenyl butyric acid | 4% | 35% | 16% | 10% | <2% | 18% |
| Ethyl pyruvate | 60% | 560% | 148% | 122% | 480% | 160% |
| Ethyl phenylglyoxylate | 8% | 35% | 3% | 4% | <2% | 11% |
| Ethyl-4-chloro acetoacetate | 79% | 70% | 100% | 80% | 110% | 110% |
| Methyl acetoacetate | 100% | 100% | 100% | 100% | 100% | 100% |
| Ethyl-3-oxovaleriate | 60% | 45% | 73% | 30% | <2% | 56% |
| Acetone | 82% | 55% | 100% | 28% | <2% | 7% |

7f Stability in the Aqueous/Organic Two-Phase System

The stability of the novel oxidoreductases in aqueous/organic two-phase systems was examined by diluting the lysates obtained in Example 6 (from a recombinant expression) in an aqueous buffer suitable for the respective oxidoreductase (approx. 10 units/ml buffer). Then, the same volume of an organic solvent not miscible with water was added to the oxidoreductase diluted in the buffer and the batch was incubated at room temperature with constant thorough mixing (thermomixer at 170 rpm). After 24 h of incubation, 10 ill each were taken from the aqueous phase and used for the determination of the enzyme activity in the standard test batch (potassium phosphate buffer (KPP) 100 mM, pH=7.0, 0.2 mM NAD(P)H, 10 mM substrate). Also in this case, the initial value immediately after the dilution in the buffer was set to 100%, and all further values were put in relation thereto.

TABLE 9

Enzyme activity after 24 h of incubation in the aqueous/organic two-phase system

| System | Buffer | Butyl-acetate | Diethyl-ether | MTBE | Diisopropyl-ether | Heptane | Cyclohexane |
| --- | --- | --- | --- | --- | --- | --- | --- |
| Rhodotorula mucilaginosa SEQ ID No 1 | 100% | 80-100% | 80-100% | 80-100% | 80-100% | 80-100% | 80-100% |
| Pichia farinosa SEQ ID No 2 | 100% | 40-60 | 60-80% | 80-100% | 40-60% | 40-60 | 40-60% |
| Candida nemodendra SEQ ID No 8 | 100% | 80-100% | 80-100% | 80-100% | 80-100% | 80-100% | 80-100% |
| Pichia stipidis SEQ ID No 3 | 100% | 40-60% | n.b. | 20-50% | 60-80% | 80-100% | 40-60% |

TABLE 9-continued

Enzyme activity after 24 h of incubation in the aqueous/organic two-phase system

| System | Buffer | Butyl-acetate | Diethyl-ether | MTBE | Diiso-propyl-ether | Heptane | Cyclo-hexane |
|---|---|---|---|---|---|---|---|
| Leuconostoc carnosum SEQ ID No 4 | 100% | 80-100% | 80-100% | 80-100% | 80-100% | 80-100% | 80-100% |
| Microbacterium spec. SEQ ID No 5 | 100% | 80-100% | 80-100% | 80-100% | 80-100% | 80-100% | 80-100% |
| Gordonia rubripertincta SEQ ID No 6 | 100% | 80-100% | 80-100% | 80-100% | 80-100% | 80-100% | 80-100% |

MTBE = Methyl-tert-butyl ether

TABLE 10

Substrate spectra oxidation

| Substrate | Rhodotorula mucilaginosa SEQ ID NO 1 | Pichia farinosa SEQ ID NO 2 | Pichia stipidis SEQ ID NO 3 | Leuconostoc carnosum SEQ ID NO 4 | Microbacterium spec. SEQ ID NO 5 | Gordonia rubripertincta SEQ ID NO 6 |
|---|---|---|---|---|---|---|
| S-2-Octanol | 100% | 0% | 100% | 0% | 100% | 100% |
| R-2-Octanol | 0% | 100% | 0% | 100% | 0% | 0% |
| S-2-Butanol | 266% | 100% | 237% | 56% | 5% | 45% |
| R-2-Butanol | 60% | 340% | 74% | 178% | 0% | 17% |
| S-Phenyl-2-propanol | 200% | 0% | 26% | 0% | 10% | 0% |
| R-Phenyl-2-propanol | 0% | 0% | 0% | 6% | 0% | 0% |
| Ethyl-(S)-4-chloro-3-hydroxy-butyrate | 0% | 0% | 0% | 0% | 0% | 0% |
| Ethyl-(R)-4-chloro-3-hydroxy-butyrate | 0% | 0% | 0% | 0% | 10% | 0% |
| 2-Propanol | 180% | 180% | 218% | 67% | <1% | 27% |
| Cyclohexanol | 26% | 120% | 0% | n.b. | n.b. | 7% |

Example 8

Preparative Conversions

8a: Synthesis of methyl-(3S)-3-hydroxypentanoate with oxidoreductase from *Rhodotorula mucilaginosa*

For the preparative batch, a mixture of 25 ml of a buffer (100 mM TEA, pH=7, 1 mM ZnCl$_2$, 10% glycerol), 375 ml 4-methyl-2-pentanol, 100 ml methyl-3-oxopentanoate, 100 mg NAD and 37 kU recombinant oxidoreductase from *Rhodotorula mucillaginosa* DSMZ 70825 was incubated at room temperature for 24 h with constant thorough mixing. After 24 h, 97% of the methyl-3-oxopentanoate used had been reduced to methyl-(3S)-3-hydroxypentanoate. Subsequently, the 4-methyl-2-pentanol phase containing the product was separated from the aqueous phase, filtered, and the product methyl-(3S)-3-hydroxypentanoate was obtained by distillation.

In this manner, the product methyl-(3S)-3-hydroxypentanoate was obtained in high yield with a purity of >99% and with an enantiomeric excess of >99.5%.

8b: Synthesis of (2R)-1-chloropropane-2-ol with oxidoreductase from *Pichia farinosa*

For the conversion, a mixture of 80 ml of a buffer (100 mM TEA, pH=7, 1 mM MgCl2, 10% glycerol), 15 ml 2-propanol, 5 ml chloroacetone, 10 mg NAD and 2 kU recombinant oxidoreductase from *Pichia farinosa* DSMZ 3316 was incubated at room temperature for 24 h with constant thorough mixing. After 24 h, the chloroacetone used had been reduced completely to (2R)-1-chloropropane-2-ol. Subsequently, the reaction mixture was extracted with ethyl acetate, the solvent was removed using a rotary evaporator, and the crude product was obtained. The (2R)-1-chloropropane-2-ol produced in this manner has an enantiomeric excess of >99%.

8c: Synthesis of (R)-2-chloro-1-(3-chlorophenyl) ethane-1-ol with oxidoreductase from *Pichia stipidis*

For the conversion, a mixture of 20 ml of a buffer (100 mM potassium phosphate, pH=8.5, 1 mM MgCl$_2$, 10% glycerol), 20 g 2-chloro-1-(3-chlorophenyl)ethane-1-one dissolved in 80 ml 4-methyl-2-pentanol, 10 mg NAD and 20 000 U recombinant oxidoreductase from *Pichia stipidis* DSMZ 3651 was incubated at room temperature for 24 h with constant thorough mixing. After 24 h, more than 99% of the 2-chloro-1-(3-chlorophenyl)ethane-1-one used had been reduced. Subsequently, the 4-methyl-2-pentanol phase containing the product was separated from the aqueous phase, filtered, and the product (R)-2-chloro-1-(3-chlorophenyl)ethane-1-ol was obtained by distillation.

In this manner, the product (R)-2-chloro-1-(3-chlorophenyl)ethane-1-ol was obtained in high yield with a purity of >98% and with an enantiomeric excess of >99.9%.

8d: Synthesis of ethyl-(S)-4-chloro-3-hydroxybutyric acid with oxidoreductase from *Leuconostoc carnosum*

For the conversion, a mixture of 8 mL of a buffer (100 mM TEA, pH=7, 1 mM MgCl$_2$), 24 ml isopropanol, 8 ml ethyl-4-chloroacetoacetate, 2 mg NADP and 6.7 kU (=6 ml) recombinant oxidoreductase from *Leuconostoc* carnosum DSMZ 5576 was incubated at room temperature for 24 h with constant thorough mixing. After 24 h, more than 99% of the ethyl-4-chloroacetoacetate used had been reduced to ethyl-(S)-4-chloro-3-hydroxybutyric acid. The reaction mixture was reprocessed by first removing the 2-propanol using a rotary evaporator. Subsequently, the reaction mixture was extracted with ethyl acetate, the solvent was removed using a rotary evaporator, and the crude product was obtained. The crude product ethyl-(S)-4-chloro-3-hydroxybutyric acid obtained in this manner exhibited an enantiomeric excess of >99.5%.

8e: Synthesis of (1S)-1-0,5-bis(trifluoromethyl)phenyl ethane-1-ol with oxidoreductase from *Microbacterium* spec.

For the conversion, a mixture of 1 mL of a buffer (100 mM TEA, pH=7, 10% glycerol, 1 mM $ZnCl_2$), 3 ml 4-methyl-2-pentanol, 1 ml 1-[3,5 bis-(trifluoro-methyl)phenyl]ethane-1-one, 2 mg NAD and 0.7 kU recombinant oxidoreductase from *Microbacterium* spec. DSMZ 20028 was incubated at room temperature for 24 h with constant thorough mixing. After 24 h, more than 90% of the 1-[3,5 bis-(trifluoro-methyl)phenyl]ethane-1-one used had been reduced to (1S)-1[3,5-bis(trifluoromethyephenyl)ethane-1-ol. Subsequently, the 4-methyl2-pentanol phase containing the product was separated from the aqueous phase, filtered, and the product (1S)-1[3,5-bis(trifluoromethyl)phenyl]ethane-1-ol was obtained by distillation. The crude product (1S)-1-[3,5-bis(trifluoromethyl)phenyl]ethane-1-one obtained in this manner exhibited an enantiomeric excess of >99.5%.

---

The invention claimed is:

1. A recombinant host cell which is a bacterial, insect, plant or isolated mammalian cell and has been transformed or transfected with an expression vector comprising:
a nucleic acid sequence encoding an oxidoreductase and which is linked to an expression control sequence, wherein the oxidoreductase has an amino acid sequence at least 70% identical to SEQ ID No:6 or fragment thereof and reduces 2-octanone to (S)-2-octanol and/or 4-haloacetoacetate ester to (R)-4-halo-3-hydroxybutyric ester in the presence of NADH or NADPH with enantiomeric purity of more than 95%.

2. The recombinant host cell according to claim 1, wherein the oxidoreductase is enzymatically active for the enantioselective enzymatic reduction of 2-octanone to (S)-2-octanol with enantiomeric purity of 100%.

3. The recombinant host cell according to claim 1, wherein the oxidoreductase is enzymatically active for the enantioselective enzymatic reduction of 4-haloacetoacetate ester to (R)-4-halo-3-hydroxybutyric ester with enantiomeric purity of 100%.

4. An expression vector comprising:
a nucleic acid sequence encoding an oxidoreductase and is linked to an expression control sequence, wherein the codes for an oxidoreductase has an amino acid sequence at least 70% identical to SEQ ID No:6 or fragment thereof and reduces 2-octanone to (S)-2-octanol and/or 4-haloacetoacetate ester to (R)-4-halo-3-hydroxybutyric ester in the presence of NADH or NADPH with enantiomeric purity of more than 95%.

5. The expression vector of claim 4, wherein the oxidoreductase is enzymatically active for the enantioselective enzymatic reduction of 2-octanone to (S)-2-octanol with enantiomeric purity of 100%.

6. The expression vector according to claim 4, wherein the oxidoreductase is enzymatically active for the enantioselective enzymatic reduction of 4-haloacetoacetate ester to (R)-4-halo-3-hydroxybutyric ester with enantiomeric purity of 100%.

7. A cloning vector comprising:
a nucleic acid sequence encoding an oxidoreductase having an amino acid sequence at least 70% identical to SEQ ID No:6 or fragment thereof, wherein said oxidoreductase reduces 2-octanone to (S)-2-octanol and/or 4-haloacetoacetate ester to (R)-4-halo-3-hydroxybutyric ester in the presence of NADH or NADPH with enantiomeric purity of more than 95%.

8. The cloning vector of claim 7, wherein the oxidoreductase is enzymatically active for the enantioselective enzymatic reduction of 2-octanone to (S)-2-octanol with enantiomeric purity of 100%.

9. The cloning vector of claim 7, wherein the oxidoreductase is enzymatically active for the enantioselective enzymatic reduction of 4-haloacetoacetate ester to (R)-4-halo-3-hydroxybutyric ester with enantiomeric purity of 100%.

10. A recombinant host cell which is a bacterial, insect, plant or isolated mammalian cell and has been transformed or transfected with an expression vector comprising a nucleic acid sequence encoding an oxidoreductase having an amino acid sequence of at least 95% identical to SEQ ID No:6 or enzymatically active fragment thereof.

11. An expression vector comprising a nucleic acid sequence encoding an oxidoreductase having an amino acid sequence at least 95% identical to SEQ ID No:6 or enzymatically active fragment thereof.

12. A cloning vector comprising a nucleic acid sequence encoding an oxidoreductase having an amino acid sequence at least 95% identical to SEQ ID No:6 or enzymatically active fragment thereof.

13. A process for the enantioselective enzymatic reduction of a keto compound to the corresponding chiral hydroxy compound comprising contacting the keto compound with an oxidoreductase having an amino acid sequence at least 95% identical to SEQ ID NO:6 or enzymatically active fragment thereof and NADP or NADPH, wherein the keto compound is reduced to the corresponding alcohol.

* * * * *

UNITED STATES PATENT AND TRADEMARK OFFICE
CERTIFICATE OF CORRECTION

| | | |
|---|---|---|
| PATENT NO. | : 9,040,265 B2 | Page 1 of 1 |
| APPLICATION NO. | : 13/280876 | |
| DATED | : May 26, 2015 | |
| INVENTOR(S) | : Tschentscher et al. | |

It is certified that error appears in the above-identified patent and that said Letters Patent is hereby corrected as shown below:

In the Claims

<u>Column 95, Claim 4</u>
Line 3-4, change "the codes for an" to --the codes for the--

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 130

<210> SEQ ID NO 1
<211> LENGTH: 282
<212> TYPE: PRT
<213> ORGANISM: Rhodotorula mucilaginosa

<400> SEQUENCE: 1

```
Met Pro Ala Thr Leu Arg Leu Asp Lys Lys Val Ala Ile Ile Thr Gly
1               5                   10                  15

Gly Ala Ser Gly Ile Gly Leu Glu Ser Ala Leu Val Phe Ala Gly Glu
            20                  25                  30

Gly Ala His Val Val Val Ala Asp Ile Asn Val Glu Ala Ala Asn Arg
        35                  40                  45

Ala Val Glu Ile Ile Lys Thr Gln Val Gln Asp Ala Pro Lys Ala Ile
    50                  55                  60

Ala Val Lys Cys Asp Val Ser Lys Glu Asp Asp Ile Lys Asn Leu Val
65                  70                  75                  80

Ala Thr Ala Val Glu Thr Phe Gly Arg Leu Asp Val Met Phe Asn Asn
                85                  90                  95

Ala Gly Ile Met His Pro Glu Asp Asp Asn Ala Leu Asn Thr Ser Glu
            100                 105                 110

Arg Ile Trp Asp Leu Thr Met Asn Ile Asn Val Lys Gly Val Trp Trp
        115                 120                 125

Gly Cys Lys Tyr Ala Ile Asp Ala Met Arg Lys Asn Pro Gly Gly Ser
    130                 135                 140

Lys Gly Ser Ile Ile Asn Thr Ala Ser Phe Val Ala Ile Leu Gly Ala
145                 150                 155                 160

Ala Thr Pro Gln Ile Ala Tyr Thr Ala Ser Lys Gly Ala Val Leu Ala
                165                 170                 175

Met Thr Arg Glu Leu Ala Met Val His Ala Arg Glu Gly Ile Arg Ile
            180                 185                 190

Asn Ser Leu Cys Pro Gly Pro Leu Lys Thr Glu Leu Leu Met Lys Phe
        195                 200                 205

Leu Asp Thr Pro Glu Lys Lys Glu Arg Arg Met Val His Ile Pro Met
    210                 215                 220

Gly Arg Phe Gly Glu Ala Val Glu Gln Ala Arg Ala Ala Phe Leu
225                 230                 235                 240

Ala Ser Asp Asp Ser Ser Phe Ile Thr Gly Thr Asp Phe Lys Val Asp
                245                 250                 255

Gly Gly Ile Ser Ser Cys Tyr Val Thr Pro Glu Gly Glu Gln Ala Leu
            260                 265                 270

Ala Ala Pro Ser Asn Leu Ala Pro Lys Ala
        275                 280
```

```
<210> SEQ ID NO 2
<211> LENGTH: 254
<212> TYPE: PRT
<213> ORGANISM: Pichia farinosa

<400> SEQUENCE: 2

Met Ala Tyr Asn Phe Thr Asn Lys Val Ala Ile Ile Thr Gly Gly Ile
1               5                   10                  15

Ser Gly Ile Gly Leu Ala Thr Val Glu Lys Phe Ala Lys Leu Gly Ala
            20                  25                  30

Lys Val Val Ile Gly Asp Ile Gln Lys Glu Glu Tyr Lys Glu Ala Ala
        35                  40                  45

Phe Thr Asn Leu Lys Asn Lys Gly Ile Asn Leu Asp Gln Leu Thr Tyr
    50                  55                  60

Val His Thr Asp Val Thr Ala Asn Ser Ala Asn Glu Asn Leu Leu Lys
65                  70                  75                  80

Thr Ala Ile Ser Ser Phe Gly Gly Val Asp Phe Val Val Ala Asn Ser
                85                  90                  95

Gly Ile Ala Lys Asp Gln Arg Ser Glu Glu Met Thr Tyr Glu Asp Phe
            100                 105                 110

Lys Lys Ile Ile Asp Val Asn Leu Asn Gly Val Phe Ser Leu Asp Lys
        115                 120                 125

Leu Ala Ile Asp Tyr Trp Leu Lys Asn Lys Lys Gly Ser Ile Val
    130                 135                 140

Asn Thr Gly Ser Ile Leu Ser Phe Val Gly Thr Pro Gly Leu Ser His
145                 150                 155                 160

Tyr Cys Ala Ser Lys Gly Gly Val Lys Leu Leu Thr Gln Thr Leu Ala
                165                 170                 175

Leu Glu Gln Ala Lys Asn Gly Ile Arg Val Asn Cys Ile Asn Pro Gly
            180                 185                 190

Tyr Ile Arg Thr Pro Leu Leu Glu Phe Leu Pro Lys Asp Lys Tyr Asp
        195                 200                 205

Ala Leu Val Asp Leu His Pro Met Gly Arg Leu Gly Glu Pro Glu Glu
    210                 215                 220

Ile Ala Asn Ala Ile Ala Phe Leu Val Ser Asp Glu Ala Ser Phe Ile
225                 230                 235                 240

Thr Gly Thr Thr Leu Leu Val Asp Gly Gly Tyr Thr Ala Gln
                245                 250

<210> SEQ ID NO 3
<211> LENGTH: 336
<212> TYPE: PRT
<213> ORGANISM: Pichia stipitis

<400> SEQUENCE: 3

Met Ser Ile Pro Ala Thr Gln Tyr Gly Phe Val Phe Thr Lys Lys Asp
1               5                   10                  15

Gly Leu Lys Ile Arg Glu Asn Met Pro Val Leu Glu Pro Lys Ala Asp
            20                  25                  30

Gln Val Leu Leu Lys Val Asp Ala Val Gly Leu Cys His Ser Asp Leu
        35                  40                  45

His Ala Ile Tyr Asp Gly Phe Asp Phe Gly Asp Asn Tyr Val Met Gly
    50                  55                  60

His Glu Ile Ala Gly Thr Ile Val Lys Lys Gly Ala Met Val Asp Phe
65                  70                  75                  80
```

```
Trp Asp Leu Asn Thr Arg Val Ala Cys Phe Gly Pro Asn Ser Cys Gly
            85                  90                  95

His Cys Gln Leu Cys Arg Thr Gly Phe Glu Asn Asp Cys Ile Asn Val
        100                 105                 110

Val Asn Gly Trp Phe Gly Leu Gly Lys Asn Gly Gly Tyr Gln Gln Tyr
        115                 120                 125

Leu Leu Val Glu Lys Pro Arg Asn Leu Val Ala Ile Pro Asp Asn Val
    130                 135                 140

Glu Leu Ser Asp Ala Ala Ile Thr Asp Ala Leu Leu Thr Pro Tyr
145                 150                 155                 160

His Ala Met Arg Leu Ala Gly Val Arg Ser Gly Thr Lys Leu Leu Gln
                165                 170                 175

Ile Gly Ala Gly Gly Leu Gly Val Asn Gly Ile Gln Ile Ala Lys Ala
                180                 185                 190

Phe Gly Ala Gln Val Thr Val Ile Asp Lys Lys Pro Glu Ala Val Asp
                195                 200                 205

Val Ala Lys Ser Leu Gly Ala Asp Glu Val Tyr Ser Ala Leu Pro Glu
    210                 215                 220

Ser Thr Ser Pro Gly Ser Phe Asp Val Ala Ile Asp Tyr Val Ser Thr
225                 230                 235                 240

Gln Gly Thr Phe Asp Thr Cys Gln Lys Tyr Val Arg Ser Lys Gly Asn
                245                 250                 255

Ile Val Pro Val Gly Leu Ala Ala Pro Arg Ile Ser Phe Asn Leu Gly
                260                 265                 270

Asp Leu Ala Leu Arg Glu Ile Asn Val Leu Gly Ser Phe Trp Gly Thr
                275                 280                 285

Ser Ser Asp Leu Lys Glu Cys Phe Asp Leu Val Ser Lys Gly Lys Val
        290                 295                 300

Lys Pro Lys Val Thr Val Ala Pro Leu Lys Gln Leu Pro Glu Tyr Ile
305                 310                 315                 320

Val Lys Leu Gln Asn Ser Ala Tyr Glu Gly Arg Val Val Phe Lys Pro
                325                 330                 335
```

<210> SEQ ID NO 4
<211> LENGTH: 252
<212> TYPE: PRT
<213> ORGANISM: Leuconostoc carnosum

<400> SEQUENCE: 4

```
Met Thr Asp Arg Leu Lys Asn Lys Val Ala Ile Ile Thr Gly Gly Thr
1               5                   10                  15

Leu Gly Ile Gly Leu Ala Met Ala Gln Lys Phe Val Glu Glu Gly Ala
                20                  25                  30

Lys Val Val Ile Thr Gly Arg Arg Ala Asn Val Gly Ala Glu Ala Leu
            35                  40                  45

Lys Thr Ile Gly Asp Glu Ser Val Ala Arg Phe Val Gln His Asp Ala
        50                  55                  60

Ser Asp Glu Lys Gly Trp Ile Asp Leu Phe Glu Asn Thr Ile Lys Trp
65                  70                  75                  80

Phe Gly His Val Asp Thr Val Val Asn Asn Ala Gly Val Ala Ile Ala
                85                  90                  95

Lys Asn Ile Glu Glu Thr Thr Tyr Glu Asp Trp Lys Phe Leu Gln Ser
            100                 105                 110

Ile Asn Ser Asp Gly Val Phe Leu Gly Thr Lys Tyr Gly Met Gln Tyr
        115                 120                 125
```

Met Lys Asn Gln Ala Gly Gly Ala Ser Ile Ile Asn Met Ser Ser Ile
130                 135                 140

Glu Gly Phe Val Gly Asp Pro Asn Leu Ala Ala Tyr Asn His Ser Lys
145                 150                 155                 160

Gly Gly Val Arg Ile Leu Ser Lys Ser Ala Ala Leu His Ala Ala Leu
            165                 170                 175

Asn Asp Tyr Asn Leu Arg Val Asn Thr Ile His Pro Gly Tyr Ile Lys
        180                 185                 190

Thr Pro Leu Val Asp Gly Ile Asp Gly Ala Glu Ala Gln Ser Gln
    195                 200                 205

Arg Thr Gln Thr Pro Met Gly His Ile Gly Glu Pro Asn Asp Ile Ala
210                 215                 220

Tyr Met Ala Val Tyr Leu Ala Ser Glu Ser Lys Phe Ala Thr Gly
225                 230                 235                 240

Ala Glu Phe Val Val Asp Gly Gly Tyr Leu Ala Gln
            245                 250

<210> SEQ ID NO 5
<211> LENGTH: 347
<212> TYPE: PRT
<213> ORGANISM: Microbacterium sp.

<400> SEQUENCE: 5

Met Lys Ala Leu Gln Tyr Thr Lys Ile Gly Ser His Pro Glu Val Val
1               5                   10                  15

Glu Ile Glu Lys Pro Ser Pro Gly Pro Gly Gln Val Leu Leu Lys Val
            20                  25                  30

Thr Ala Ala Gly Val Cys His Ser Asp Glu Phe Val Met Ser Leu Ser
        35                  40                  45

Glu Glu Gln Tyr Thr Ala Ala Gly Tyr Pro Leu Pro Leu Thr Leu Gly
    50                  55                  60

His Glu Gly Ala Gly Ile Val Glu Glu Leu Gly Glu Gly Val Glu His
65                  70                  75                  80

Leu Ser Val Gly Asp Ala Val Ala Val Tyr Gly Pro Trp Gly Cys Gly
                85                  90                  95

Arg Cys Arg Asn Cys Ala Gln Gly Lys Glu Asn Tyr Cys Thr Asn Ala
            100                 105                 110

Gln Ala Glu Gly Ile Met Pro Pro Gly Leu Gly Ala Pro Gly Ser Met
        115                 120                 125

Ala Glu Tyr Met Ile Val Asp Ser Ala Arg His Leu Val Pro Leu Gly
130                 135                 140

Asp Leu Asp Pro Val Gln Asn Val Ser Leu Thr Asp Ala Gly Leu Thr
145                 150                 155                 160

Pro Tyr His Ala Val Lys Thr Ser Leu Pro Lys Leu Gly Ala Gly Thr
            165                 170                 175

Thr Ala Val Val Ile Gly Thr Gly Gly Leu Gly His Val Ala Ile Gln
        180                 185                 190

Ile Leu Arg Ala Val Ser Ala Ala Thr Val Ile Ala Leu Asp Val Asn
    195                 200                 205

Asp Glu Lys Leu Ala Leu Ala Lys Glu Val Gly Ala His His Thr Val
210                 215                 220

Met Ser Asp Gly Gly Ala Val Asp Ala Ile Arg Arg Leu Thr Asp Gly
225                 230                 235                 240

Leu Gly Ala Asn Ala Val Phe Asp Phe Val Gly Ala Asp Pro Thr Ile

```
                    245                 250                 255
Ala Thr Ala Ile Gly Ala Ala Ala Leu Asp Ala Asp Ile Thr Ile Val
                260                 265                 270

Gly Ile Gly Gly Gly Thr Ala His Val Gly Phe Gly Thr Val Ala Tyr
            275                 280                 285

Asp Ala Ala Leu Arg Ile Pro Tyr Trp Gly Ser Arg Ser Glu Leu Ile
        290                 295                 300

Glu Val Leu Asp Leu Ala Arg Ser Gly Gln Val Gly Val Glu Ile Gln
305                 310                 315                 320

Arg Tyr Ser Leu Asp Asp Gly Pro Lys Ala Tyr Glu Ala Leu Ala Ala
                325                 330                 335

Gly Thr Val Arg Gly Arg Ala Val Ile Val Pro
                340                 345

<210> SEQ ID NO 6
<211> LENGTH: 347
<212> TYPE: PRT
<213> ORGANISM: Gordonia rubripertincta

<400> SEQUENCE: 6

Met Lys Ala Ile Gln Ile Ile Gln Pro Gly Lys Pro Pro Glu Leu Arg
1               5                   10                  15

Glu Val Glu Lys Pro Thr Pro Arg Pro Gly Gln Val Leu Leu Lys Val
            20                  25                  30

Thr Ala Ala Gly Ala Cys His Ser Asp Asp Phe Val Leu Asn Leu Pro
        35                  40                  45

Glu Glu Gly Phe Pro Tyr Pro Leu Pro Met Thr Leu Gly His Glu Gly
    50                  55                  60

Ala Gly Val Val Ala Glu Val Gly Thr Gly Val Thr Gly Ile Ser Glu
65                  70                  75                  80

Gly Thr Ser Val Ala Val Tyr Gly Ala Trp Gly Cys Gly Val Cys His
                85                  90                  95

Phe Cys Ala Arg Gly Leu Glu Asn Tyr Cys Ser Arg Ala Gly Glu Leu
            100                 105                 110

Gly Ile Thr Pro Pro Gly Leu Gly Asn Pro Gly Ala Met Ala Glu Tyr
        115                 120                 125

Leu Leu Val Asp Asp Ala Arg His Leu Val Pro Leu Gly Asp Leu Asp
    130                 135                 140

Pro Val Ala Ala Val Pro Leu Thr Asp Ala Gly Leu Thr Pro Tyr His
145                 150                 155                 160

Ala Ile Lys Pro Ser Leu Pro Lys Leu Val Gly Gly Thr Thr Ala Val
                165                 170                 175

Val Ile Gly Ala Gly Gly Leu Gly His Val Gly Ile Gln Leu Leu Arg
            180                 185                 190

His Leu Thr Pro Ser Arg Val Ile Ala Leu Asp Val Ser Asp Asp Lys
        195                 200                 205

Leu Ala Phe Ala Arg Glu Val Gly Ala His Glu Val Leu Ser Asp
    210                 215                 220

Ala Asp Ala Val Ala Asn Val Arg Lys Ile Thr Gly Asn Asp Gly Ala
225                 230                 235                 240

Thr Ala Val Phe Asp Phe Val Gly Leu Gln Pro Thr Leu Asp Ile Ala
                245                 250                 255

Met Gly Val Val Gly Thr Met Gly Asp Val Val Ile Val Gly Ile Gly
            260                 265                 270
```

Asp Met Val Ala Thr Ala Lys Val Gly Phe Phe Thr Gln Pro Tyr Glu
            275                 280                 285

Val Ser Val Arg Ala Pro Tyr Trp Gly Ala Arg Asp Glu Leu Ile Glu
        290                 295                 300

Val Leu Asp Leu Ala Arg Asp Gly Val Leu Glu Val Ala Val Glu Arg
305                 310                 315                 320

Phe Ser Leu Asp Asp Gly Val Glu Ala Tyr Arg Arg Leu Ala Ala Asn
                325                 330                 335

Asp Leu Arg Gly Arg Ala Val Val Pro Asp
            340                 345

<210> SEQ ID NO 7
<211> LENGTH: 339
<212> TYPE: PRT
<213> ORGANISM: Pichia trehalophila

<400> SEQUENCE: 7

Met Cys Thr Ser Gln Ser Gly Tyr Val Tyr His Ser Gly Arg Pro Leu
1               5                   10                  15

Leu Thr Lys Glu Glu Leu Ser Ile Pro Glu Pro Lys Gly Ser Glu Ile
            20                  25                  30

Val Leu Lys Val Arg Ala Ala Gly Leu Cys Ser Ser Asp Val His Val
        35                  40                  45

Leu Asn Ser Ser Leu Pro Leu Thr Tyr Pro Asn Ser Phe Ala Met Gly
    50                  55                  60

His Glu Ile Ala Gly Glu Ile Tyr Lys Leu Gly Pro Asn Val Asp Ala
65                  70                  75                  80

Asp Lys Tyr Ser Ile Gly Asp Gly Tyr Ala Val His Gly Leu Asn Ser
                85                  90                  95

Cys Gly Asp Cys Ser Phe Cys Lys Val Gly Ser Gln Asn Leu Cys Thr
            100                 105                 110

Asp Asn Asn Ser Thr Trp Tyr Gly Leu Gly Lys Asn Gly Gly Tyr Glu
        115                 120                 125

Gln Tyr Val Leu Val Lys Ser Val His Asp Leu Ile Lys Ile Pro Glu
    130                 135                 140

Gly Val Ser Phe Ser Glu Ala Val Ala Ser Asp Ala Val Leu Thr
145                 150                 155                 160

Pro Tyr His Ala Ile Ser Thr Cys Asn Leu Lys Ala Thr Ser Lys Val
                165                 170                 175

Leu Val Ile Gly Cys Gly Gly Leu Gly Thr Cys Ala Leu Gln Ile Ile
            180                 185                 190

Lys Leu Tyr Ser Ala Tyr Val Val Cys Val Asp Ser Lys Ala Glu Leu
        195                 200                 205

Glu Glu Leu Ala Lys Glu Tyr Gly Ala Asp Glu Phe Tyr Thr Asp Leu
    210                 215                 220

Ser Lys Ser Ser Val Pro Lys Met Ser Phe Asp Cys Val Phe Asp Phe
225                 230                 235                 240

Val Ala Ile Gln Pro Thr Phe Thr Ile Ser Gln Asn Tyr Val Lys Ser
                245                 250                 255

Gly Gly Ile Ile Lys Pro Val Leu Gly Ala Pro Ser Leu Thr Phe
            260                 265                 270

Ser Leu Leu Asp Leu Gly Cys Arg Asp Val Lys Ile Ile Gly Ser Phe
        275                 280                 285

Trp Gly Thr Gln Ala Glu Gln Lys Asp Cys Met Glu Leu Ile Gln Arg
    290                 295                 300

```
Gly Leu Val Lys Pro Leu Ile Thr Ser Phe Thr Phe Asp Glu Phe Pro
305                 310                 315                 320

Gln Ala Tyr Glu Leu Leu Ser Thr Gly Lys Ser Lys Gly Arg Leu Val
            325                 330                 335

Ile Ser Gln

<210> SEQ ID NO 8
<211> LENGTH: 254
<212> TYPE: PRT
<213> ORGANISM: Candida nemodendra

<400> SEQUENCE: 8

Met Gly Tyr Asn Leu Ile Asn Lys Val Ala Val Thr Gly Gly Cys
1               5                   10                  15

Ser Gly Ile Gly Leu Ala Val Thr Lys Lys Tyr Leu Glu Leu Gly Ala
            20                  25                  30

Lys Val Val Ile Gly Asp Val Ser Thr Lys Glu Lys Phe Asn Glu Val
            35                  40                  45

Ser Ser Glu Leu Lys Val Ala Gly Leu Asn Val Asn Asn Leu Asn Phe
50                  55                  60

Val Ser Ala Asp Ser Ser Lys Glu Asp Asn Lys Arg Leu Val Asp
65                  70                  75                  80

Glu Ala Ile Lys Asn Phe Gly Gly Leu Asp Ile Val Cys Ala Asn Ala
                85                  90                  95

Gly Ile Gly Ser Met Ile Pro Phe His Glu Met Thr Phe Glu Ala Trp
            100                 105                 110

Arg Lys Leu Leu Ala Val Asn Leu Asp Gly Val Phe Leu Leu Asp Arg
            115                 120                 125

Phe Ala Ile Asp Tyr Trp Leu Lys Asn Ser Lys Pro Gly Val Ile Val
        130                 135                 140

Asn Met Gly Ser Ile His Ser Phe Val Ala Ala Pro Gly Leu Ala His
145                 150                 155                 160

Tyr Ser Ala Ser Lys Gly Gly Val Lys Leu Leu Thr Glu Ala Leu Ala
                165                 170                 175

Leu Glu Tyr Ser Ser Lys Gly Ile Arg Val Asn Ser Val Asn Pro Ala
            180                 185                 190

Tyr Ile Gln Thr Ser Leu Leu Glu Phe Leu Pro Glu Asp Lys Met Asn
        195                 200                 205

Ala Leu Lys Ala Val His Pro Ile Gly Arg Leu Gly Lys Pro Glu Glu
    210                 215                 220

Val Ala Asn Ala Val Ala Phe Leu Ser Ser Asp Glu Ala Thr Phe Ile
225                 230                 235                 240

His Gly Thr Ser Leu Leu Val Asp Gly Gly Tyr Thr Ala Gln
                245                 250

<210> SEQ ID NO 9
<211> LENGTH: 849
<212> TYPE: DNA
<213> ORGANISM: Rhodotorula mucilaginosa
<220> FEATURE:
<221> NAME/KEY: gene
<222> LOCATION: (1)..(849)

<400> SEQUENCE: 9
atgcctgcca ctctccgcct cgacaagaag gttgccatca tcaccggagg agcatccggg     60
atcggcctcg agtcggccct cgtctttgcc ggagaaggcg cccacgtcgt cgtcgccgac    120
```

| | |
|---|---|
| atcaacgtcg aagctgccaa ccgcgccgtc gagatcatca agacccaggt tcaggacgcc | 180 |
| cccaaggcga tcgccgtcaa gtgcgacgtc tccaaggagg acgacatcaa gaacctcgtc | 240 |
| gcgactgctg tcgaaacttt tggcaggctc gatgtcatgt tcaacaacgc cggcatcatg | 300 |
| caccccgagg acgacaatgc gctcaacacc tcggagcgca tctgggacct gaccatgaac | 360 |
| attaacgtca agggagtctg tgggggctgc aagtacgcga tcgacgccat gcgcaagaac | 420 |
| ccgggcggca gcaaggggag catcatcaac acggcttcgt tcgtcgccat cctcggagcg | 480 |
| gcgacgcctc agatcgcata caccgcttcg aagggtgccg tcttggccat gactcgcgag | 540 |
| ctcgccatgg ttcacgcgcg cgaagggatc cgaatcaact cgctctgccc cggtccgctc | 600 |
| aagacagagc tcctgatgaa gttcctcgac acgccggaga agaaggagcg ccggatggtg | 660 |
| cacatcccga tgggtcgctt cggtgaggcg gttgagcagg ctcgcgcggc cgcgttcctc | 720 |
| gctagcgacg acagcagctt catcaccgga actgacttca aggtcgacgg cggtatcagc | 780 |
| tcgtgctacg tcacgccgga gggcgagcag gccctcgcgg cgccgtccaa cttggctccc | 840 |
| aaggcgtag | 849 |

<210> SEQ ID NO 10
<211> LENGTH: 765
<212> TYPE: DNA
<213> ORGANISM: Pichia farinosa
<220> FEATURE:
<221> NAME/KEY: gene
<222> LOCATION: (1)..(765)

<400> SEQUENCE: 10

| | |
|---|---|
| atggcctata acttcactaa caaagtcgct atcattacag gaggaatttc cggtattggt | 60 |
| ttagctacag tcgagaaatt cgctaagttg ggtgctaaag tcgtcatagg agacattcaa | 120 |
| aaagaagaat ataaagaagc tgcttttaca aatttgaaga caaaggaat taatcttgat | 180 |
| caattgacgt atgtccacac ggacgtcacc gcaaattcgg caaatgagaa cctttttaaag | 240 |
| actgctataa gctccttttgg tggcgttgac tttgtcgtag caaactctgg aatagcaaaa | 300 |
| gatcaacgtt ctgaagagat gacttatgaa gatttcaaga aaataatcga tgtcaactta | 360 |
| aacggtgttt tttccttgga taagctagca attgattatt ggttaaaaaa taagaaaaag | 420 |
| ggctctattg tcaacacggg atctattctt tcatttgttg gtaccccgg gttatcacat | 480 |
| tattgtgcgt caagggtgg agtgaagtta ttgacacaaa ccttggctct cgaacaggct | 540 |
| aagaatggca taagagtgaa ttgtatatat cctggttata taagaacacc tttattagag | 600 |
| tttttgccta aggacaagta tgacgcttta gtggatcttc atccaatggg tagattaggt | 660 |
| gaacctgagg aaattgccaa tgccattgca ttcctcgtct ctgacgaagc gagcttcata | 720 |
| actggtacta ctctactcgt tgatggagga tatacagccc agtaa | 765 |

<210> SEQ ID NO 11
<211> LENGTH: 1011
<212> TYPE: DNA
<213> ORGANISM: Pichia stipitis
<220> FEATURE:
<221> NAME/KEY: gene
<222> LOCATION: (1)..(1011)

<400> SEQUENCE: 11

| | |
|---|---|
| atgtctattc ctgctacaca atatggtttc gtcttcacca aaaaggacgg tttaaaaatt | 60 |
| cgcgagaaca tgcctgttct cgaacccaag gctgaccaag tcttgcttaa agtcgacgca | 120 |

```
gtaggattgt gtcactctga ccttcatgcc atctacgacg gcttcgactt tggtgacaat      180
tacgttatgg gccacgaaat cgccggcacc attgtcaaga agggagccat ggtcgacttt      240
tgggacctaa acacccgtgt tgcctgtttt ggtccaaact cctgtggcca ttgtcaactt      300
tgtcgtactg gttttgaaaa tgattgtatc aatgtcgtca acggctggtt tggattaggt      360
aaaaacggag gctaccagca atatttgttg gttgaaaagc ctcgtaattt ggttgctatt      420
ccagacaacg tcgagctgtc cgatgcagct gccattaccg acgctttgtt gacccctac       480 catgccatga gattagctgg tgttagatca ggcacgaagc tcttgcaaat tggtgctgga      540
ggattgggag taaatggtat tcagattgct aaagcatttg gagctcaagt cactgttatc      600
gacaaaaagc ccgaggctgt agacgtcgct aagagcctag gcgcagatga agtatattct      660
gcacttcctg aatcaaccag tccgggaagt ttcgatgttg ctatcgacta cgtttctact      720
caaggcactt tcgacacttg tcaaaagtac gtcagatcta agggtaatat tgttcccgtt      780
ggattggccg ctccaagaat ttcgtttaac ttgggagatt tggcccttag agaaattaat      840
gtccttggta gcttctgggg tacatcatcc gacttgaagg aatgtttcga tttggtcagc      900
aagggcaaag tcaaacctaa ggtgactgtt gctccattga agcaattgcc tgaatacatt      960
gtcaagttac agaattcggc ctacgaaggt agagtcgtgt tcaagccatg a              1011

<210> SEQ ID NO 12
<211> LENGTH: 759
<212> TYPE: DNA
<213> ORGANISM: Leuconostoc carnosum
<220> FEATURE:
<221> NAME/KEY: gene
<222> LOCATION: (1)..(759)

<400> SEQUENCE: 12
atgacagatc ggttaaagaa taaagttgct attatcactg gtggtacact tggtattggc       60
ttagcaatgg ctcaaaagtt tgtagaagaa ggcgctaaag ttgtcattac tgggcgtcgt      120
gctaatgttg gtgcagaagc gctaaagaca attggtgatg aatcagtagc acgatttgtt      180
caacatgatg catctgatga aaaaggctgg attgatttat ttgaaaatac gattaaatgg      240
tttggtcatg tcgatacggt tgtcaataat gccggtgttg caattgctaa aaacattgaa      300
gagacaacat atgaagactg gaaattttg caatcaatca actctgatgg cgttttctta      360
ggaactaagt acggtatgca atatatgaaa accaagctg gtggtgcctc aattattaat      420
atgtcatcta ttgaaggatt tgttggtgat cctaacttag ctgcttataa tcattcaaaa      480
ggtggtgtcc gcattttgag taagtcagct gcactacatg cagcattgaa tgactataac      540
ttacgtgtca cacgattca cccaggatat atcaaaacac cattggttga tggtattgat      600
ggtgcagaag aagcccaatc acaaagaact caaacaccta tgggacatat tggtgaacct      660
aatgatattg catatatggc agtctatta gctagtgaag aatcaaagtt tgcaacaggt      720
gctgaattcg ttgttgatgg cggctatttg gcacaataa                             759

<210> SEQ ID NO 13
<211> LENGTH: 1044
<212> TYPE: DNA
<213> ORGANISM: Microbacterium sp.
<220> FEATURE:
<221> NAME/KEY: gene
<222> LOCATION: (1)..(1044)

<400> SEQUENCE: 13
atgaaggcac tccagtacac gaagatcgga tcccaccccg aagtcgtcga gatcgagaag       60
```

| | |
|---|---|
| ccctcgccgg gtcccgggca ggtactgctc aaagtcaccg ccgccggcgt ctgccactcg | 120 |
| gacgagttcg tgatgagcct cagcgaggag cagtacaccg ctgccggcta ccccctgccg | 180 |
| ctcaccctcg ggcacgaagg cgccggcatc gtcgaggagc tcggcgaagg tgtcgagcac | 240 |
| ctgagcgtcg gagacgccgt cgccgtctac ggccccctggg gttgcggccg ctgccgcaac | 300 |
| tgcgcgcagg gcaaggagaa ctactgcacg aacgcccagg cggaggggat catgcctccc | 360 |
| ggtctcgggg ctcccggctc aatggcggag tacatgatcg tcgacagcgc gcgacacctc | 420 |
| gttccgctcg gcgacctcga ccccgtgcag aacgtttcct tgacggatgc cggcctgacc | 480 |
| ccgtaccacg cggtcaagac gtcacttccg aagctgggcg ccggaacgac ggcggtcgtg | 540 |
| atcggcaccg ggggtctcgg acacgtcgcg attcagatcc tgcgggcggt gtcggccgcg | 600 |
| accgtgatcg cgttggacgt caacgacgag aaactcgcgc tggccaagga ggtcggcgcc | 660 |
| catcacaccg tcatgagcga cggcggcgcc gtcgacgcga ttcgccggct caccgacggt | 720 |
| ctgggcgcga acgccgtctt cgacttcgtc ggtgcggacc cgacgatcgc gacggcgata | 780 |
| ggagcagccg cgctcgacgc agacatcacg atcgtcggca tcggcggcgg aacggctcac | 840 |
| gtcggttttcg gcaccgtcgc ttatgacgcg gcgcttcgca tcccgtattg gggctcgcgc | 900 |
| agcgaactga tcgaggtgct cgacctcgcg cgctcagggc aggtgggagt cgagatccag | 960 |
| cgctactcac tcgacgacgg cccgaaggcg tacgaggcgc tcgccgcggg cacggtccgc | 1020 |
| ggccgcgccg tcatcgtccc ctga | 1044 |

<210> SEQ ID NO 14
<211> LENGTH: 1047
<212> TYPE: DNA
<213> ORGANISM: Gordonia rubripertincta
<220> FEATURE:
<221> NAME/KEY: gene
<222> LOCATION: (1)..(1047)

<400> SEQUENCE: 14

| | |
|---|---|
| atgatgaagg ccattcagat catccagccg ggcaaaccgc cggagctgcg cgaggtcgag | 60 |
| aaacccacgc cgcgtcccgg gcaggtgttg ctgaaggtga cggcagccgg cgcctgccat | 120 |
| tcggacgact tcgtcctcaa cctgcccgag gaaggattcc cctatcccct gccgatgacg | 180 |
| ctcggccacg aaggggccgg cgtggtcgcc gaggtcggta ccggcgtcac ggcatctcc | 240 |
| gagggcacct cggtggccgt gtacggagcc tggggttgcg gcgtctgtca cttctgcgcc | 300 |
| cgcggcctgg agaactactg cagccgagcc ggcgaactcg gcatcacccc accgggtctc | 360 |
| ggcaacccgg gcgcgatggc cgagtacctg ctcgtggacg acgcacggca tctggtgccg | 420 |
| ctcggtgacc tcgacccggt ggctgcagtc ccactcaccg atgccggcct cacgccctac | 480 |
| cacgcgatca aaccctcgct tccgaagctg gtcgcggca ccacggcagt ggtcatcgga | 540 |
| gccggtggtc tcgggcatgt cgggatccaa ctgcttcgcc acctgacccc gtcccgggtg | 600 |
| atcgctctcg acgtgagcga cgacaagctc gcgttcgcgc gcgaggtcgg ggctcacgag | 660 |
| gtggtgctct ccgacgccga tgccgtcgcg aacgtccgca agatcaccgg caacgatggt | 720 |
| gcgaccgccg tcttcgactt cgtcgggctg caacccacgc tcgacatcgc gatgggcgtc | 780 |
| gtcgggacca tgggtgacgt ggtgatcgtg ggcatcggtg acatggtcgc cacggcgaag | 840 |
| gtcggcttct tcacccagcc ctacgaggtg tcggtacgcg cgccgtactg ggggcgcgc | 900 |
| gacgaactca tcgaggtgct ggatctcgca cgcgatgggg ttctcgaggt ggcggtcgaa | 960 |
| cgattctcac tcgatgacgg cgtcgaggcc taccggcgac tggccgccaa tgaccttcga | 1020 |

```
gggcgagcag tcgtggtgcc tgactga                                        1047
```

<210> SEQ ID NO 15
<211> LENGTH: 1020
<212> TYPE: DNA
<213> ORGANISM: Pichia trehalophila
<220> FEATURE:
<221> NAME/KEY: gene
<222> LOCATION: (1)..(1020)

<400> SEQUENCE: 15

```
atgtgtactt ctcaatctgg ctacgtttat cattctggta gaccactttt aactaaagaa   60
gaactttcaa ttcccgaacc aaaaggctct gaaattgttc taaaagttcg tgcagctggt  120
ttatgttcat cagatgttca tgttctaaac agcagtttac cattgactta cccaaacagt  180
tttgctatgg gtcatgaaat tgccggtgaa atttataagc ttggtccaaa cgttgacgct  240
gataaatatt caattggaga tggatatgca gttcatggtt tgaactcctg tggtgattgt  300
tccttctgta aggttggtag tcaaaacctg tgtaccgata caattcaac ttggtacggg  360
ttaggtaaga tggtggtta tgaacagtac gttttagtta aaagtgttca tgacttaatt  420
aaaattccag aaggtgttag tttctcagag gccgcagttg cttcagatgc tgttttaact  480
ccatatcatg ctatcagcac ctgtaacttg aaggcaactt ccaaagtttt agttattggt  540
tgtggtgggt taggtacctg tgctttacaa atcatcaaat tgtacagtgc atatgttgtc  600
tgtgttgact ccaaagcaga attagaagaa cttgctaaag aatatggcgc tgatgaattc  660
tacaccgatt tatcaaaatc cagcgttccc aaaatgtcat tgattgtgt ttttgatttt  720
gttgccattc agccaacttt caccatttct caaaattacg tcaagagcgg tggtatcatc  780
aaacctgttg gcttaggtgc tcctagctta acatttagtt tattggactt aggttgtaga  840
gacgttaaga tcattggctc tttctggggt acacaagctg aacaaaaaga ctgtatggaa  900
ctaattcaaa gaggtttagt caagccatta attacaagtt tcactttga tgaatttcct  960
caagcttatg aattgttgtc gactgggaaa tccaagggta gattggttat cagtcaatag 1020
```

<210> SEQ ID NO 16
<211> LENGTH: 765
<212> TYPE: DNA
<213> ORGANISM: Candida nemodendra
<220> FEATURE:
<221> NAME/KEY: gene
<222> LOCATION: (1)..(765)

<400> SEQUENCE: 16

```
atgggttaca acttaatcaa caaagttgca gtcgtcacag gaggctgctc cggaattggt   60
ctcgcagtga ccaaaaaata tcttgaactg ggagcaaaag tggtcatagg agatgtatcc  120
actaaagaga agtttaacga ggtatcctcg gaactcaaag ttgcaggcct aaatgtaaac  180
aatttaaact tgtttcagc agacagtagc aaagaagacg acaacaaacg tttagttgac  240
gaagcaatca agaactttgg tggtcttgat attgtgtgtg ctaatgccgg tatcggtagc  300
atgattccat ccatgaaaat gacatttgaa gcatggagaa agttactcgc agtaaacctt  360
gatggtgtgt tcttgctaga cagattcgca attgattact ggttaaagaa tagcaaacct  420
ggtgttatcg tcaacatggg ttcaatccac tctttcgtcg ctgctccagg attagcacat  480
tactctgctt ccaagggagg tgtcaaacta ttgaccgaag ctcttgctct agagtactcg  540
tccaagggta ttagagtaaa ttctgtgaat cctgcatata ttcaaacctc attgctagaa  600
```

```
ttccttccag aagacaaaat gaatgccttg aaggcggtgc accctattgg ccgtttaggt      660
aaaccagaag aagtagccaa tgctgtcgca ttcctcagtt ccgatgaagc aaccttcata      720
catggtactt ctcttctagt tgatggaggt tacaccgctc aataa                      765
```

<210> SEQ ID NO 17
<211> LENGTH: 9
<212> TYPE: PRT
<213> ORGANISM: Rhodotorula mucilaginosa
<220> FEATURE:
<221> NAME/KEY: PEPTIDE
<222> LOCATION: (1)..(9)

<400> SEQUENCE: 17

```
Met Pro Ala Thr Leu Arg Leu Asp Lys
1               5
```

<210> SEQ ID NO 18
<211> LENGTH: 13
<212> TYPE: PRT
<213> ORGANISM: Rhodotorula mucilaginosa
<220> FEATURE:
<221> NAME/KEY: PEPTIDE
<222> LOCATION: (1)..(13)

<400> SEQUENCE: 18

```
Gln Ala Leu Ala Ala Pro Ser Asn Leu Ala Pro Lys Ala
1               5                   10
```

<210> SEQ ID NO 19
<211> LENGTH: 10
<212> TYPE: PRT
<213> ORGANISM: Rhodotorula mucilaginosa
<220> FEATURE:
<221> NAME/KEY: PEPTIDE
<222> LOCATION: (1)..(10)

<400> SEQUENCE: 19

```
Val Glu Ile Ile Lys Thr Gln Val Gln Asp
1               5                   10
```

<210> SEQ ID NO 20
<211> LENGTH: 14
<212> TYPE: PRT
<213> ORGANISM: Rhodotorula mucilaginosa
<220> FEATURE:
<221> NAME/KEY: PEPTIDE
<222> LOCATION: (1)..(14)

<400> SEQUENCE: 20

```
Lys Val Ala Ile Ile Thr Gly Gly Ala Ser Gly Ile Gly Leu
1               5                   10
```

<210> SEQ ID NO 21
<211> LENGTH: 8
<212> TYPE: PRT
<213> ORGANISM: Rhodotorula mucilaginosa
<220> FEATURE:
<221> NAME/KEY: PEPTIDE
<222> LOCATION: (1)..(8)

<400> SEQUENCE: 21

```
Ser Cys Tyr Val Thr Pro Glu Gly
1               5
```

<210> SEQ ID NO 22
<211> LENGTH: 8

```
<212> TYPE: PRT
<213> ORGANISM: Rhodotorula mucilaginosa
<220> FEATURE:
<221> NAME/KEY: PEPTIDE
<222> LOCATION: (1)..(8)

<400> SEQUENCE: 22

Thr Asp Phe Lys Val Asp Gly Gly
1               5

<210> SEQ ID NO 23
<211> LENGTH: 10
<212> TYPE: PRT
<213> ORGANISM: Rhodotorula mucilaginosa
<220> FEATURE:
<221> NAME/KEY: PEPTIDE
<222> LOCATION: (1)..(10)

<400> SEQUENCE: 23

Val Met Phe Asn Asn Ala Gly Ile Met His
1               5                   10

<210> SEQ ID NO 24
<211> LENGTH: 10
<212> TYPE: PRT
<213> ORGANISM: Rhodotorula mucilaginosa
<220> FEATURE:
<221> NAME/KEY: PEPTIDE
<222> LOCATION: (1)..(10)

<400> SEQUENCE: 24

Val His Ala Arg Glu Gly Ile Arg Ile Asn
1               5                   10

<210> SEQ ID NO 25
<211> LENGTH: 10
<212> TYPE: PRT
<213> ORGANISM: Pichia farinosa
<220> FEATURE:
<221> NAME/KEY: PEPTIDE
<222> LOCATION: (1)..(10)

<400> SEQUENCE: 25

Met Ala Tyr Asn Phe Thr Asn Lys Val Ala
1               5                   10

<210> SEQ ID NO 26
<211> LENGTH: 12
<212> TYPE: PRT
<213> ORGANISM: Pichia farinosa
<220> FEATURE:
<221> NAME/KEY: PEPTIDE
<222> LOCATION: (1)..(12)

<400> SEQUENCE: 26

Thr Thr Leu Leu Val Asp Gly Gly Tyr Thr Ala Gln
1               5                   10

<210> SEQ ID NO 27
<211> LENGTH: 9
<212> TYPE: PRT
<213> ORGANISM: Pichia farinosa
<220> FEATURE:
<221> NAME/KEY: PEPTIDE
<222> LOCATION: (1)..(9)

<400> SEQUENCE: 27

Glu Tyr Lys Glu Ala Ala Phe Thr Asn
```

-continued

<210> SEQ ID NO 28
<211> LENGTH: 16
<212> TYPE: PRT
<213> ORGANISM: Pichia farinosa
<220> FEATURE:
<221> NAME/KEY: PEPTIDE
<222> LOCATION: (1)..(16)

<400> SEQUENCE: 28

Asn Lys Val Ala Ile Ile Thr Gly Gly Ile Ser Gly Ile Gly Leu Ala
1               5                   10                  15

<210> SEQ ID NO 29
<211> LENGTH: 9
<212> TYPE: PRT
<213> ORGANISM: Pichia farinosa
<220> FEATURE:
<221> NAME/KEY: PEPTIDE
<222> LOCATION: (1)..(9)

<400> SEQUENCE: 29

Asp Val Asn Leu Asn Gly Val Phe Ser
1               5

<210> SEQ ID NO 30
<211> LENGTH: 9
<212> TYPE: PRT
<213> ORGANISM: Pichia farinosa
<220> FEATURE:
<221> NAME/KEY: PEPTIDE
<222> LOCATION: (1)..(9)

<400> SEQUENCE: 30

His Tyr Cys Ala Ser Lys Gly Gly Val
1               5

<210> SEQ ID NO 31
<211> LENGTH: 8
<212> TYPE: PRT
<213> ORGANISM: Pichia farinosa
<220> FEATURE:
<221> NAME/KEY: PEPTIDE
<222> LOCATION: (1)..(8)

<400> SEQUENCE: 31

Asn Cys Ile Asn Pro Gly Tyr Ile
1               5

<210> SEQ ID NO 32
<211> LENGTH: 9
<212> TYPE: PRT
<213> ORGANISM: Pichia farinosa
<220> FEATURE:
<221> NAME/KEY: PEPTIDE
<222> LOCATION: (1)..(9)

<400> SEQUENCE: 32

Leu His Pro Met Gly Arg Leu Gly Glu
1               5

<210> SEQ ID NO 33
<211> LENGTH: 11
<212> TYPE: PRT
<213> ORGANISM: Pichia stipitis
<220> FEATURE:
<221> NAME/KEY: PEPTIDE

```
<222> LOCATION: (1)..(11)

<400> SEQUENCE: 33

Met Ser Ile Pro Ala Thr Gln Tyr Gly Phe Val
1               5                   10

<210> SEQ ID NO 34
<211> LENGTH: 11
<212> TYPE: PRT
<213> ORGANISM: Pichia stipitis
<220> FEATURE:
<221> NAME/KEY: PEPTIDE
<222> LOCATION: (1)..(11)

<400> SEQUENCE: 34

Ser Ala Tyr Glu Gly Arg Val Val Phe Lys Pro
1               5                   10

<210> SEQ ID NO 35
<211> LENGTH: 9
<212> TYPE: PRT
<213> ORGANISM: Pichia stipitis
<220> FEATURE:
<221> NAME/KEY: PEPTIDE
<222> LOCATION: (1)..(9)

<400> SEQUENCE: 35

Cys His Ser Asp Leu His Ala Ile Tyr
1               5

<210> SEQ ID NO 36
<211> LENGTH: 9
<212> TYPE: PRT
<213> ORGANISM: Pichia stipitis
<220> FEATURE:
<221> NAME/KEY: PEPTIDE
<222> LOCATION: (1)..(9)

<400> SEQUENCE: 36

Gly Tyr Gln Gln Tyr Leu Leu Val Glu
1               5

<210> SEQ ID NO 37
<211> LENGTH: 9
<212> TYPE: PRT
<213> ORGANISM: Pichia stipitis
<220> FEATURE:
<221> NAME/KEY: PEPTIDE
<222> LOCATION: (1)..(9)

<400> SEQUENCE: 37

Thr Phe Asp Thr Cys Gln Lys Tyr Val
1               5

<210> SEQ ID NO 38
<211> LENGTH: 8
<212> TYPE: PRT
<213> ORGANISM: Pichia stipitis
<220> FEATURE:
<221> NAME/KEY: PEPTIDE
<222> LOCATION: (1)..(8)

<400> SEQUENCE: 38

Leu Leu Thr Pro Tyr His Ala Met
1               5

<210> SEQ ID NO 39
```

```
<211> LENGTH: 9
<212> TYPE: PRT
<213> ORGANISM: Pichia stipitis
<220> FEATURE:
<221> NAME/KEY: PEPTIDE
<222> LOCATION: (1)..(9)

<400> SEQUENCE: 39

Leu Val Ser Lys Gly Lys Val Lys Pro
1               5

<210> SEQ ID NO 40
<211> LENGTH: 9
<212> TYPE: PRT
<213> ORGANISM: Pichia stipitis
<220> FEATURE:
<221> NAME/KEY: PEPTIDE
<222> LOCATION: (1)..(9)

<400> SEQUENCE: 40

Gly Ala Gly Gly Leu Gly Val Asn Gly
1               5

<210> SEQ ID NO 41
<211> LENGTH: 10
<212> TYPE: PRT
<213> ORGANISM: Pichia stipitis
<220> FEATURE:
<221> NAME/KEY: PEPTIDE
<222> LOCATION: (1)..(10)

<400> SEQUENCE: 41

Ile Gln Ile Ala Lys Ala Phe Gly Ala Thr
1               5                   10

<210> SEQ ID NO 42
<211> LENGTH: 8
<212> TYPE: PRT
<213> ORGANISM: Pichia stipitis
<220> FEATURE:
<221> NAME/KEY: PEPTIDE
<222> LOCATION: (1)..(8)

<400> SEQUENCE: 42

Leu Gly Ser Phe Trp Gly Thr Ser
1               5

<210> SEQ ID NO 43
<211> LENGTH: 10
<212> TYPE: PRT
<213> ORGANISM: Leuconostoc carnosum
<220> FEATURE:
<221> NAME/KEY: PEPTIDE
<222> LOCATION: (1)..(10)

<400> SEQUENCE: 43

Met Thr Asp Arg Leu Lys Asn Lys Val Ala
1               5                   10

<210> SEQ ID NO 44
<211> LENGTH: 12
<212> TYPE: PRT
<213> ORGANISM: Leuconostoc carnosum
<220> FEATURE:
<221> NAME/KEY: PEPTIDE
<222> LOCATION: (1)..(12)

<400> SEQUENCE: 44
```

```
Ala Glu Phe Val Val Asp Gly Gly Tyr Leu Ala Gln
1               5                   10

<210> SEQ ID NO 45
<211> LENGTH: 9
<212> TYPE: PRT
<213> ORGANISM: Leuconostoc carnosum
<220> FEATURE:
<221> NAME/KEY: PEPTIDE
<222> LOCATION: (1)..(9)

<400> SEQUENCE: 45

Val Val Ile Thr Gly Arg Arg Ala Asn
1               5

<210> SEQ ID NO 46
<211> LENGTH: 9
<212> TYPE: PRT
<213> ORGANISM: Leuconostoc carnosum
<220> FEATURE:
<221> NAME/KEY: PEPTIDE
<222> LOCATION: (1)..(9)

<400> SEQUENCE: 46

Gly Gly Ala Ser Ile Ile Asn Met Ser
1               5

<210> SEQ ID NO 47
<211> LENGTH: 8
<212> TYPE: PRT
<213> ORGANISM: Leuconostoc carnosum
<220> FEATURE:
<221> NAME/KEY: PEPTIDE
<222> LOCATION: (1)..(8)

<400> SEQUENCE: 47

Thr Gln Thr Pro Met Gly His Ile
1               5

<210> SEQ ID NO 48
<211> LENGTH: 10
<212> TYPE: PRT
<213> ORGANISM: Leuconostoc carnosum
<220> FEATURE:
<221> NAME/KEY: PEPTIDE
<222> LOCATION: (1)..(10)

<400> SEQUENCE: 48

Gly Tyr Ile Lys Thr Pro Leu Val Asp Gly
1               5                   10

<210> SEQ ID NO 49
<211> LENGTH: 11
<212> TYPE: PRT
<213> ORGANISM: Microbacterium sp.
<220> FEATURE:
<221> NAME/KEY: PEPTIDE
<222> LOCATION: (1)..(11)

<400> SEQUENCE: 49

Met Lys Ala Leu Gln Tyr Thr Lys Ile Gly Ser
1               5                   10

<210> SEQ ID NO 50
<211> LENGTH: 14
<212> TYPE: PRT
<213> ORGANISM: Microbacterium sp.
<220> FEATURE:
```

```
<221> NAME/KEY: PEPTIDE
<222> LOCATION: (1)..(14)

<400> SEQUENCE: 50

Leu Ala Ala Gly Thr Val Arg Gly Arg Ala Val Ile Val Pro
1               5                   10

<210> SEQ ID NO 51
<211> LENGTH: 12
<212> TYPE: PRT
<213> ORGANISM: Microbacterium sp.
<220> FEATURE:
<221> NAME/KEY: PEPTIDE
<222> LOCATION: (1)..(12)

<400> SEQUENCE: 51

Cys His Ser Asp Glu Phe Val Met Ser Leu Ser Glu
1               5                   10

<210> SEQ ID NO 52
<211> LENGTH: 10
<212> TYPE: PRT
<213> ORGANISM: Microbacterium sp.
<220> FEATURE:
<221> NAME/KEY: PEPTIDE
<222> LOCATION: (1)..(10)

<400> SEQUENCE: 52

Val Tyr Gly Pro Trp Gly Cys Gly Arg Cys
1               5                   10

<210> SEQ ID NO 53
<211> LENGTH: 13
<212> TYPE: PRT
<213> ORGANISM: Microbacterium sp.
<220> FEATURE:
<221> NAME/KEY: PEPTIDE
<222> LOCATION: (1)..(13)

<400> SEQUENCE: 53

Val Ser Leu Thr Asp Ala Gly Leu Thr Pro Tyr His Ala
1               5                   10

<210> SEQ ID NO 54
<211> LENGTH: 12
<212> TYPE: PRT
<213> ORGANISM: Microbacterium sp.
<220> FEATURE:
<221> NAME/KEY: PEPTIDE
<222> LOCATION: (1)..(12)

<400> SEQUENCE: 54

Leu Arg Ala Val Ser Ala Ala Thr Val Ile Ala Leu
1               5                   10

<210> SEQ ID NO 55
<211> LENGTH: 9
<212> TYPE: PRT
<213> ORGANISM: Microbacterium sp.
<220> FEATURE:
<221> NAME/KEY: PEPTIDE
<222> LOCATION: (1)..(9)

<400> SEQUENCE: 55

Asp Phe Val Gly Ala Asp Pro Thr Ile
1               5
```

```
<210> SEQ ID NO 56
<211> LENGTH: 8
<212> TYPE: PRT
<213> ORGANISM: Gordonia rubripertincta
<220> FEATURE:
<221> NAME/KEY: PEPTIDE
<222> LOCATION: (1)..(8)

<400> SEQUENCE: 56

Met Lys Ala Ile Gln Ile Ile Gln
1               5

<210> SEQ ID NO 57
<211> LENGTH: 10
<212> TYPE: PRT
<213> ORGANISM: Gordonia rubripertincta
<220> FEATURE:
<221> NAME/KEY: PEPTIDE
<222> LOCATION: (1)..(10)

<400> SEQUENCE: 57

Asp Leu Arg Gly Arg Ala Val Val Val Pro
1               5                   10

<210> SEQ ID NO 58
<211> LENGTH: 9
<212> TYPE: PRT
<213> ORGANISM: Gordonia rubripertincta
<220> FEATURE:
<221> NAME/KEY: PEPTIDE
<222> LOCATION: (1)..(9)

<400> SEQUENCE: 58

Thr Ala Ala Gly Ala Cys His Ser Asp
1               5

<210> SEQ ID NO 59
<211> LENGTH: 11
<212> TYPE: PRT
<213> ORGANISM: Gordonia rubripertincta
<220> FEATURE:
<221> NAME/KEY: PEPTIDE
<222> LOCATION: (1)..(11)

<400> SEQUENCE: 59

Thr Pro Tyr His Ala Ile Lys Pro Ser Leu Pro
1               5                   10

<210> SEQ ID NO 60
<211> LENGTH: 8
<212> TYPE: PRT
<213> ORGANISM: Gordonia rubripertincta
<220> FEATURE:
<221> NAME/KEY: PEPTIDE
<222> LOCATION: (1)..(8)

<400> SEQUENCE: 60

Asp Phe Val Gly Leu Gln Pro Thr
1               5

<210> SEQ ID NO 61
<211> LENGTH: 8
<212> TYPE: PRT
<213> ORGANISM: Gordonia rubripertincta
<220> FEATURE:
<221> NAME/KEY: PEPTIDE
<222> LOCATION: (1)..(8)

<400> SEQUENCE: 61
```

```
Val Tyr Gly Ala Trp Gly Cys Gly
1               5
```

<210> SEQ ID NO 62
<211> LENGTH: 8
<212> TYPE: PRT
<213> ORGANISM: Gordonia rubripertincta
<220> FEATURE:
<221> NAME/KEY: PEPTIDE
<222> LOCATION: (1)..(8)

<400> SEQUENCE: 62

```
Asp Asp Ala Arg His Leu Val Pro
1               5
```

<210> SEQ ID NO 63
<211> LENGTH: 8
<212> TYPE: PRT
<213> ORGANISM: Gordonia rubripertincta
<220> FEATURE:
<221> NAME/KEY: PEPTIDE
<222> LOCATION: (1)..(8)

<400> SEQUENCE: 63

```
Met Thr Leu Gly His Glu Gly Ala
1               5
```

<210> SEQ ID NO 64
<211> LENGTH: 14
<212> TYPE: PRT
<213> ORGANISM: Gordonia rubripertincta
<220> FEATURE:
<221> NAME/KEY: PEPTIDE
<222> LOCATION: (1)..(14)

<400> SEQUENCE: 64

```
Gly Gly Leu Gly His Val Gly Ile Gln Leu Leu Arg His Leu
1               5                   10
```

<210> SEQ ID NO 65
<211> LENGTH: 18
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(18)

<400> SEQUENCE: 65

```
caggaaacag ctatgacc                                                  18
```

<210> SEQ ID NO 66
<211> LENGTH: 10
<212> TYPE: PRT
<213> ORGANISM: Rhodotorula mucilaginosa
<220> FEATURE:
<221> NAME/KEY: PEPTIDE
<222> LOCATION: (1)..(10)

<400> SEQUENCE: 66

```
Val Ala Thr Ala Val Glu Thr Phe Gly Arg
1               5                   10
```

<210> SEQ ID NO 67
<211> LENGTH: 9
<212> TYPE: PRT

```
<213> ORGANISM: Rhodotorula mucilaginosa
<220> FEATURE:
<221> NAME/KEY: PEPTIDE
<222> LOCATION: (1)..(9)

<400> SEQUENCE: 67

Phe Gly Glu Ala Val Glu Gln Ala Arg
1               5

<210> SEQ ID NO 68
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(20)

<400> SEQUENCE: 68
ccraaytcva cvgcvgtsgc                                         20

<210> SEQ ID NO 69
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(20)

<400> SEQUENCE: 69
gcctgytcga cvgcytcrcc                                         20

<210> SEQ ID NO 70
<211> LENGTH: 22
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(22)

<400> SEQUENCE: 70
ctccgaggtg ttgagcgcat tg                                      22

<210> SEQ ID NO 71
<211> LENGTH: 25
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(25)

<400> SEQUENCE: 71
gacgaggttc ttgatgtcgt cctcc                                   25

<210> SEQ ID NO 72
<211> LENGTH: 12
<212> TYPE: PRT
<213> ORGANISM: Pichia farinosa
<220> FEATURE:
<221> NAME/KEY: PEPTIDE
<222> LOCATION: (1)..(12)
```

-continued

```
<400> SEQUENCE: 72

Leu Leu Thr Gln Thr Leu Ala Leu Glu Gln Ala Lys
1               5                   10

<210> SEQ ID NO 73
<211> LENGTH: 14
<212> TYPE: PRT
<213> ORGANISM: Pichia farinosa
<220> FEATURE:
<221> NAME/KEY: PEPTIDE
<222> LOCATION: (1)..(14)

<400> SEQUENCE: 73

Tyr Asn Phe Thr Asn Lys Val Ala Ile Ile Thr Gly Gly Ile
1               5                   10

<210> SEQ ID NO 74
<211> LENGTH: 21
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(21)
<220> FEATURE:
<221> NAME/KEY: misc_feature
<222> LOCATION: (10)..(10)
<223> OTHER INFORMATION: n is a, c, g, or t

<400> SEQUENCE: 74
ytgytcyaan gcyaadgtyt g                                         21

<210> SEQ ID NO 75
<211> LENGTH: 25
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(25)
<220> FEATURE:
<221> NAME/KEY: misc_feature
<222> LOCATION: (11)..(11)
<223> OTHER INFORMATION: n is a, c, g, or t

<400> SEQUENCE: 75
chaayaargt ngchathaty achgg                                     25

<210> SEQ ID NO 76
<211> LENGTH: 25
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(25)

<400> SEQUENCE: 76
caacgttctg aagagatgac ttatg                                     25

<210> SEQ ID NO 77
<211> LENGTH: 20
<212> TYPE: DNA
<213> ORGANISM: Artificial
<220> FEATURE:
<223> OTHER INFORMATION: synthetic construct
```

```
<220> FEATURE:
<221> NAME/KEY: misc_feature
<222> LOCATION: (1)..(20)

<400> SEQUENCE: 77
ggtggagtga agttattgac                                                      20

<210> SEQ ID NO 78
<211> LENGTH: 23
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(23)

<400> SEQUENCE: 78
gccattctta gcctgttcga gag                                                  23

<210> SEQ ID NO 79
<211> LENGTH: 25
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(25)

<400> SEQUENCE: 79
gtcatctctt cagaacgttg atctt                                                25

<210> SEQ ID NO 80
<211> LENGTH: 7
<212> TYPE: PRT
<213> ORGANISM: Pichia stipitis
<220> FEATURE:
<221> NAME/KEY: PEPTIDE
<222> LOCATION: (1)..(7)

<400> SEQUENCE: 80

Ala Asp Gln Val Leu Leu Lys
1               5

<210> SEQ ID NO 81
<211> LENGTH: 11
<212> TYPE: PRT
<213> ORGANISM: Pichia stipitis
<220> FEATURE:
<221> NAME/KEY: PEPTIDE
<222> LOCATION: (1)..(11)

<400> SEQUENCE: 81

Ile Ser Phe Asn Leu Gly Asp Leu Ala Leu Arg
1               5                   10

<210> SEQ ID NO 82
<211> LENGTH: 21
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(21)
<220> FEATURE:
<221> NAME/KEY: misc_feature
<222> LOCATION: (12)..(12)
```

<223> OTHER INFORMATION: n is a, c, g, or t

<400> SEQUENCE: 82
gcygaycarg tnttrttraa r                                              21

<210> SEQ ID NO 83
<211> LENGTH: 21
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(21)

<400> SEQUENCE: 83
ctyaargcya artcdccyaa r                                              21

<210> SEQ ID NO 84
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(20)

<400> SEQUENCE: 84
ctaccatgcc atgagattag                                                20

<210> SEQ ID NO 85
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(20)

<400> SEQUENCE: 85
gctgtagacg tcgctaagag                                                20

<210> SEQ ID NO 86
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(20)

<400> SEQUENCE: 86
gattctcaag gctaagtcac                                                20

<210> SEQ ID NO 87
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(20)

<400> SEQUENCE: 87
gatctaacac cagctaatct                                               20

<210> SEQ ID NO 88
<211> LENGTH: 22
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(22)

<400> SEQUENCE: 88
ccaaaggagc ttatagcagt ct                                            22

<210> SEQ ID NO 89
<211> LENGTH: 29
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(29)

<400> SEQUENCE: 89
gggaaattcc atatgcctgc cactctccg                                     29

<210> SEQ ID NO 90
<211> LENGTH: 33
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(33)

<400> SEQUENCE: 90
cggcaagctt attacgcctt gggagccaag ttg                                33

<210> SEQ ID NO 91
<211> LENGTH: 32
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(32)

<400> SEQUENCE: 91
ggaaattcca tatggcctat aacttcacta ac                                 32

<210> SEQ ID NO 92
<211> LENGTH: 33
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(33)

<400> SEQUENCE: 92
cactgcatgc tgatggccta aacttcact aac                                 33

<210> SEQ ID NO 93

```
<211> LENGTH: 30
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(30)

<400> SEQUENCE: 93
cgcaagctta ttactgggct gtatatcctc                                    30

<210> SEQ ID NO 94
<211> LENGTH: 33
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(33)

<400> SEQUENCE: 94
ggaaattcca tatgatgtct attcctgcta cac                                33

<210> SEQ ID NO 95
<211> LENGTH: 31
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(31)

<400> SEQUENCE: 95
cactgcatgc gaatgtctat tcctgctaca c                                  31

<210> SEQ ID NO 96
<211> LENGTH: 33
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(23)

<400> SEQUENCE: 96
cccaagctta tcatggtttg aacacgactc tac                                33

<210> SEQ ID NO 97
<211> LENGTH: 10
<212> TYPE: PRT
<213> ORGANISM: Leuconostoc carnosum
<220> FEATURE:
<221> NAME/KEY: PEPTIDE
<222> LOCATION: (1)..(10)

<400> SEQUENCE: 97

Ile Glu Glu Thr Thr Tyr Glu Asp Trp Lys
1               5                   10

<210> SEQ ID NO 98
<211> LENGTH: 27
<212> TYPE: DNA
<213> ORGANISM: Artificial
<220> FEATURE:
<223> OTHER INFORMATION: synthetic construct
```

```
<220> FEATURE:
<221> NAME/KEY: misc_feature
<222> LOCATION: (1)..(27)
<220> FEATURE:
<221> NAME/KEY: misc_feature
<222> LOCATION: (13)..(13)
<223> OTHER INFORMATION: n is a, c, g, or t

<400> SEQUENCE: 98
gacagawmgw ttnaarggwa argthgc                                              27

<210> SEQ ID NO 99
<211> LENGTH: 29
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(29)
<220> FEATURE:
<221> NAME/KEY: misc_feature
<222> LOCATION: (12)..(12)
<223> OTHER INFORMATION: n is a, c, g, or t

<400> SEQUENCE: 99
gcbgtrtawc cnccrtcdac dacraaytc                                            29

<210> SEQ ID NO 100
<211> LENGTH: 23
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(23)

<400> SEQUENCE: 100
ctaagccaat accaagtgta cca                                                  23

<210> SEQ ID NO 101
<211> LENGTH: 27
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(27)

<400> SEQUENCE: 101
gaacaaatcg tgctactgat tcatcac                                              27

<210> SEQ ID NO 102
<211> LENGTH: 25
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(25)

<400> SEQUENCE: 102
gaagaagccc aatcacaaag aactc                                                25

<210> SEQ ID NO 103
<211> LENGTH: 23
```

```
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(23)

<400> SEQUENCE: 103
ggcagtctat ttagctagtg aag                                              23

<210> SEQ ID NO 104
<211> LENGTH: 14
<212> TYPE: PRT
<213> ORGANISM: Microbacterium sp.
<220> FEATURE:
<221> NAME/KEY: PEPTIDE
<222> LOCATION: (1)..(14)

<400> SEQUENCE: 104

Met Lys Ala Leu Gln Tyr Thr Lys Ile Gly Ser His Pro Glu
1               5                   10

<210> SEQ ID NO 105
<211> LENGTH: 11
<212> TYPE: PRT
<213> ORGANISM: Microbacterium sp.
<220> FEATURE:
<221> NAME/KEY: PEPTIDE
<222> LOCATION: (1)..(11)

<400> SEQUENCE: 105

Ala Tyr Glu Ala Leu Ala Ala Gly Thr Val Val
1               5                   10

<210> SEQ ID NO 106
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(20)

<400> SEQUENCE: 106
ctscartaca cvaagatcgg                                                  20

<210> SEQ ID NO 107
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(20)

<400> SEQUENCE: 107
gcbgcsagbg cytcrtabgc                                                  20

<210> SEQ ID NO 108
<211> LENGTH: 20
<212> TYPE: DNA
<213> ORGANISM: Artificial
<220> FEATURE:
<223> OTHER INFORMATION: synthetic construct
<220> FEATURE:
<221> NAME/KEY: misc_feature
```

```
<222> LOCATION: (1)..(20)

<400> SEQUENCE: 108
tcctcgctga ggctcatcac                                                     20

<210> SEQ ID NO 109
<211> LENGTH: 22
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(22)

<400> SEQUENCE: 109
gcttctcgat ctcgacgact tc                                                  22

<210> SEQ ID NO 110
<211> LENGTH: 19
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(19)

<400> SEQUENCE: 110
gcgcagcgaa ctgatcgag                                                      19

<210> SEQ ID NO 111
<211> LENGTH: 22
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(22)

<400> SEQUENCE: 111
gatccagcgc tactcactcg ac                                                  22

<210> SEQ ID NO 112
<211> LENGTH: 10
<212> TYPE: PRT
<213> ORGANISM: Gordonia rubripertincta
<220> FEATURE:
<221> NAME/KEY: PEPTIDE
<222> LOCATION: (1)..(10)

<400> SEQUENCE: 112

Met Lys Ala Ile Gln Ile Ile Gln Pro Gly
1               5                   10

<210> SEQ ID NO 113
<211> LENGTH: 13
<212> TYPE: PRT
<213> ORGANISM: Gordonia rubripertincta
<220> FEATURE:
<221> NAME/KEY: PEPTIDE
<222> LOCATION: (1)..(13)

<400> SEQUENCE: 113

Val Gly Phe Phe Thr Gln Pro Tyr Glu Val Ser Val Arg
1               5                   10
```

<210> SEQ ID NO 114
<211> LENGTH: 26
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(26)
<220> FEATURE:
<221> NAME/KEY: misc_feature
<222> LOCATION: (9)..(9)
<223> OTHER INFORMATION: n is a, c, g, or t

<400> SEQUENCE: 114
atgaargcna tycaratyat ycarcc                                      26

<210> SEQ ID NO 115
<211> LENGTH: 22
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(22)
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 115
cytcrtangg ytgngtraar aa                                          22

<210> SEQ ID NO 116
<211> LENGTH: 21
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(21)

<400> SEQUENCE: 116
gaggacgaag tcgtccgaat g                                           21

<210> SEQ ID NO 117
<211> LENGTH: 21
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(21)

<400> SEQUENCE: 117
gccgtcacct tcagcaacac c                                           21

<210> SEQ ID NO 118
<211> LENGTH: 21
<212> TYPE: DNA
<213> ORGANISM: Artificial
<220> FEATURE:
<223> OTHER INFORMATION: synthetic construct

```
<220> FEATURE:
<221> NAME/KEY: misc_feature
<222> LOCATION: (1)..(21)

<400> SEQUENCE: 118
ctcgacgtga gcgacgacaa g                                              21

<210> SEQ ID NO 119
<211> LENGTH: 21
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(21)

<400> SEQUENCE: 119
gcaagatcac cggcaacgat g                                              21

<210> SEQ ID NO 120
<211> LENGTH: 37
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(37)

<400> SEQUENCE: 120
catatggcta gcatgacaga tcggttaaag aataaag                             37

<210> SEQ ID NO 121
<211> LENGTH: 35
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(35)

<400> SEQUENCE: 121
gcgcggatcc atgacagatc ggttaaagaa taaag                               35

<210> SEQ ID NO 122
<211> LENGTH: 29
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(29)

<400> SEQUENCE: 122
cccaagcttc ttattgtgcc aaatagccg                                      29

<210> SEQ ID NO 123
<211> LENGTH: 31
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(31)
```

<400> SEQUENCE: 123
ggaaattcca tatgaaggca ctccagtaca c                                          31

<210> SEQ ID NO 124
<211> LENGTH: 32
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(32)

<400> SEQUENCE: 124
cactgcatgc tgatgaaggc actccagtac ac                                         32

<210> SEQ ID NO 125
<211> LENGTH: 28
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(28)

<400> SEQUENCE: 125
cccaagctta acgtcagggg acgatgac                                              28

<210> SEQ ID NO 126
<211> LENGTH: 33
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(33)

<400> SEQUENCE: 126
cactgcatgc gaatgaaggc cattcagatc atc                                        33

<210> SEQ ID NO 127
<211> LENGTH: 33
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(33)

<400> SEQUENCE: 127
cccaagctta ttagtcaggc accacgactg ctc                                        33

<210> SEQ ID NO 128
<211> LENGTH: 18
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (1)..(18)

<400> SEQUENCE: 128
tgtaaaacga cggccagt                                                         18

-continued

```
<210> SEQ ID NO 129
<211> LENGTH: 336
<212> TYPE: PRT
<213> ORGANISM: Lodderomyces elongisporus

<400> SEQUENCE: 129
```

Met Ser Ile Pro Thr Thr Gln Tyr Gly Phe Val Tyr Asn Lys Ser Ser
1               5                   10                  15

Gly Leu Thr Leu Asn Lys Ser Ile Pro Val Ala Ser Ala Gly Val Gly
            20                  25                  30

Gln Leu Leu Met Lys Val Asp Ser Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Asp Val Gly Pro Glu Val Asp Arg
65                  70                  75                  80

Trp Asn Val Gly Asp Arg Val Ala Val Gly Pro Asn Gly Cys Gly
                85                  90                  95

Gly Cys Arg Ala Cys Arg Asp Gly Ile Glu Asn Val Cys Lys His Ser
            100                 105                 110

Phe Gly Asn Trp Tyr Gly Leu Gly Ser Asp Gly Gly Tyr Gln Gln Tyr
        115                 120                 125

Leu Leu Val Gln Lys Pro Arg Asn Leu Val Lys Ile Pro Asp Asn Val
    130                 135                 140

Pro Ser Asp Val Ala Ala Ser Thr Asp Ala Val Leu Thr Pro Tyr
145                 150                 155                 160

His Ala Ile Lys Met Ala Gly Val Gly Pro Thr Ser Lys Val Leu Ile
                165                 170                 175

Val Gly Ala Gly Gly Leu Gly Cys Asn Ala Val Gln Val Ala Lys Ala
            180                 185                 190

Phe Gly Ala His Val Thr Ile Leu Asp Lys Lys Glu Arg Ala Arg Ala
        195                 200                 205

Glu Ala Val Lys Phe Gly Ala Asp Val Ala Tyr Glu Ser Leu Pro Leu
    210                 215                 220

Ser Thr Glu Pro Gly Ser Phe Asp Ala Cys Leu Asp Phe Val Ser Val
225                 230                 235                 240

Gln Ala Thr Phe Gly Ile Cys Gln Lys Phe Cys Ala Pro Lys Gly Cys
                245                 250                 255

Ile Ile Pro Ala Gly Leu Gly Ala Pro Lys Leu Thr Leu Asp Leu Ala
            260                 265                 270

Asp Leu Asp Leu Arg Glu Ile Arg Ile Leu Gly Thr Phe Trp Gly Thr
    275                 280                 285

Ala Thr Asp Leu Glu Glu Val Phe Asp Leu Val Gly Lys Gly Leu Val
        290                 295                 300

Lys Pro Met Val Arg Ala Ala Lys Leu Glu Glu Leu Pro Asp Tyr Ile
305                 310                 315                 320

Glu Lys Leu Arg Lys Asn Glu Tyr Glu Gly Arg Ile Val Phe Asn Pro
                325                 330                 335

```
<210> SEQ ID NO 130
<211> LENGTH: 1011
<212> TYPE: DNA
<213> ORGANISM: Lodderomyces elongisporus
<220> FEATURE:
<221> NAME/KEY: gene
<222> LOCATION: (1)..(1011)
```

```
<400> SEQUENCE: 130
atgtcaattc caactaccca atatggtttt gtttacaata agtcgtctgg cttaacattg      60
aacaagagta tacctgttgc ctcggcaggt gtgggtcaat tgcttatgaa ggttgactct     120
gttggattgt gccactcgga cctccatgtg atttacgaag gtttggattg tggtgataac     180
tatgtcatgg gccatgagat tgccggtacc gtggttgatg ttggtccaga ggttgataga     240
tggaatgttg gtgatagagt tgccgctgtg ggtccaaatg gttgtggtgg ttgcagagcc     300
tgtcgcgacg gaattgaaaa tgtatgtaaa cactcttttg gtaattggta tggcttgggc     360
tcagatggcg gataccaaca atatttgctt gtgcaaaaac cacgcaattt ggttaagatt     420
cctgacaatg ttccttcgga tgtagctgca gcctcgactg acgctgtatt gacaccatac     480
cacgcaatca agatggctgg tgtggggcca acatcaaagg tgctcattgt tggcgctggt     540
ggcttgggct gcaatgccgt gcaagttgcc aaggcatttg gtgctcatgt cactattttg     600
gacaagaagg aacgcgcgcg cgctgaagct gtcaagtttg gtgccgacgt tgcctatgag     660
agcttaccac tgagcaccga gccaggctca tttgatgcat gtttggattt tgtttctgtg     720
caagcaacgt ttggcatttg ccaaaagttt tgtgcaccaa aaggttgcat catcccgcg      780 gggctcggtg caccaaagtt gacgcttgat ttggcagatt tggatttgcg cgaaattcgt     840
attttgggta cttttggggg aaccgcgacc gatttggagg aggtgtttga cttggttgga     900
aagggacttg ttaagcccat ggtgcgtgca gccaagttgg aggaattgcc agactatatt     960
gaaaagttga gaaagaatga atatgaaggt agaattgtct ttaatccata a              1011
```